United States Patent [19]

Martin, Jr. et al.

[11] Patent Number: 4,782,840
[45] Date of Patent: Nov. 8, 1988

[54] METHOD FOR LOCATING, DIFFERENTIATING, AND REMOVING NEOPLASMS

[75] Inventors: Edward W. Martin, Jr., Delaware; Marlin O. Thurston, Columbus, both of Ohio

[73] Assignee: Neoprobe Corporation, Columbus, Ohio

[21] Appl. No.: 905,880

[22] Filed: Sep. 10, 1986

Related U.S. Application Data

[63] Continuation-in-part of Ser. No. 585,887, Mar. 2, 1984, abandoned.

[51] Int. Cl.⁴ ............................................. A61B 10/00
[52] U.S. Cl. ..................................... 128/654; 128/659
[58] Field of Search ........................ 128/654, 659, 653

[56] References Cited

U.S. PATENT DOCUMENTS

| | | | |
|---|---|---|---|
| 3,665,916 | 5/1972 | Kobayashi et al. | 128/659 |
| 3,670,719 | 6/1972 | Kobayashi et al. | 128/659 |
| 3,827,427 | 8/1974 | Knoll | 128/659 |
| 4,015,592 | 4/1977 | Bradley-Moore | 128/659 |
| 4,092,980 | 6/1978 | Frank et al. | 128/659 |
| 4,243,884 | 1/1981 | Avera | 128/659 |
| 4,311,688 | 1/1982 | Burchiel et al. | 128/659 |
| 4,444,744 | 4/1984 | Goldenberg | 128/659 |
| 4,479,931 | 10/1984 | Lambrecht et al. | 128/659 |
| 4,595,014 | 6/1986 | Barrett et al. | 128/659 |

OTHER PUBLICATIONS

Siffert, P.: "Current Possibilities and Limitations of Cadmium Telluride Detectors", *Nuc. Inst. & Methods* 150:1–12, 1978.

Serreze, H. B.; Entine, G.; Bell, R. O.; and Wald, F. V.: "Advance in CdTe Gamma-Ray Detectors" *Trans. in Nuclear Science*, vol. NS21, No. 1, pp. 404–407 (Feb., 1974).

"Cadmium Telluride-A Breakthrough in Nuclear Radiation Detection", Marketing Brochure of Radiation Monitoring Devices, Inc., Watertown, Mass., Undated.

"Nuclear Instruments", a Marketing Brochure by Radiation Monitoring Devices, Inc., Watertown, Mass., Copyright 1981.

"A-225 Charge Sensitive Preamplifier & Shaping Amplifier", a Marketing Brochure by Amptek, Inc., Bedford, Mass., Apr. 1983.

"Technical and Clinical Characteristics of a Surgical Biopsy Probe" by Harvey and Lancaster, *Journal of Nuclear Medicine*, vol. 22, pp. 184–186, 1981.

"Role of Radionuclide Imaging in Osteoid Osteoma" by Lisbona and Rosenthall, AJR: 132, Jan. 1979.

"Scintigraphic Appearances of Osteoid Osteoma" by Smith et al., *Nuclear Medicine*, vol. 137, Oct. 1980.

"Intraoperative Skeletal Scintigraphy for Localization of Osteoid-Osteoma in the Spine", Rinsky et al., *Journal of Bone and Joint Surgery*, vol. 62-A, Jan. 1980.

"Sixty Second-Look Procedures Indicated Primarily by Rise in Serial Carcinoembryonic Antigen" by Martin, Jr. et al., *Journal of Surgical Research*, 28, 389-394 (1980).

*Primary Examiner*—Lee S. Cohen
*Assistant Examiner*—John C. Hanley
*Attorney, Agent, or Firm*—Mueller and Smith

[57] ABSTRACT

The present invention is addressed to a method for the improved localization, differentiation, and removal of neoplastic tissue in animals. In particular, one aspect of the present invention involves a surgical procedure wherein an animal suspected of containing neoplastic tissue is surgically accessed and the tissue therein examined visually and by palpation for evidence of neoplastic tissue. The improved methodology commences with the administering to the animal of an effective amount of a labelled antibody specific for neoplastic tissue and labelled with a radioactive isotope exhibiting specific photon emissions of energy levels. Next, and importantly, the surgial procedure is delayed for a time interval following said administering for permitting the labelled antibody to preferentially concentrate in any neoplastic tissue present in the animal so as to increase the ratio of photon emissions from neoplastic tissue to background photon emissions in said animal. Thereafter, an operative field of the animal is surgically accessed and tissue within the operative field to be examined for neoplastic tissue has the background photon (Abstract Continued on next page.)

emission count determined. Once the background photon emission account for tissue within the operative field has been determined, a handheld probe is manually positioned within the operative field adjacent tissue suspected of being neoplastic. The probe is configured for fascile hand positioning and maneuvering within the operative field of the animal. The probe is characterized by having a collimatable radiation detector having a selective photon entrance and having an output deriving discrete signals responsive to photon emissions when said entrance is positioned immediately adjacent thereto. The probe further comprises amplifier means having an input coupled with said radiation detector output and responsive to said discrete signals to provide corresponding amplified output pulses. Finally, the probe comprises readout means responsive to said output pulses and actuable to an initial condition for commencing the provision of a perceptible indication of an indicia corresponding to the number of said output pulses received. From the perceptible indication, the extent of tissue exhibiting a number of output pulses having a value above background output pulses is determined and such determined tissue removed surgically. Thereafter, the probe is manually positioned adjacent tissue surrounding the surgically removed tissue to determined from said perceptible indication whether any of said surrounding tissue still exhibits a number of output pulses having a value above said background output pulses. Any adjacent tissue surrounding the initial surgically removed tissue which does exhibit an increased number of output pulses is surgically removed additonally. Thereafter, the margins again are examined with the probe in order to ensure that all tissue exhibiting a number of output pulses having a value above the background output pulses has been removed.

20 Claims, 1 Drawing Sheet

METHOD FOR LOCATING, DIFFERENTIATING, AND REMOVING NEOPLASMS

CROSS-REFERENCE TO RELATED APPLICATIONS

This application is a continuation-in-part of U.S. Ser. No. 06/585,887, filed Mar. 2, 1984, now abandoned.

BACKGROUND OF THE INVENTION

This invention is concerned with the localization or differentiation of cancerous tumors or other neoplasms as they occur, for example, in colorectal cancer and additionally in dealing with other cancer occurrences.

Colorectal cancer has been the subject of extensive investigation over the past 30 years and the effort thus far has achieved little change in mortality rates. Generally, statistics have shown that from 1964 through 1973, the five-year survival rate for the illness was 77% in patients with localized cancer, and only 47% in patients with all stages of this disease. Concerning the above statistics, see the following publication:

I. "1983 Cancer Statistics", Ca-A Journal for Clinicians, published by The American Cancer Society, 33(1), 1983.

Notwithstanding the above less than desirable statistics, these lengthy investigations into the disease have evolved a variety of (a) tests, (b) of quite sophisticated radiological equipment and (c) of surgical protocols. As part of the investigations, the various, somewhat time defined, stages of colon cancer have been categorized in a sequence of A through D known as "Dukes Classification". When the colonic tumors can be found early, ie. types A and B tumors, the lesion can be isolated and the success rate for surgery is impressive. However, for more advanced tumors which are categorized at C and D levels, localization has been seen to be quite difficult and this difficulty represents a significant factor in the generation of the above statistics.

Looking to the history of the above-noted investigations, the use of radio-labelled immunoglobulin for tumor localization was shown to be possible in 1959 when Day et al. radiolabelled isolated antifibrin. See in this regard the following publication:

II. Day, E. O.; Planisek, J. A.; Pressman D: "Localization of Radioiodinated Rat Fibrinogen in Transplanted Rat Tumors", *J. Natl. Cancer Inst.* 23: 799–812, 1959.

Fibrin, while not a tumor-specific antigen, was known to have a frequency of presence in tumors due to the inflammatory process accompanying invasion. This work demonstrated that a protein in high concentration in tumor sites could be used to localize tumors. The antibodies against human fibrin and ferritin were used in attempts to employ specific immunoglobulins for diagnosis. Spar, in 1967, performed scans in 179 patients using rabbit immunospecific antifibrin antibody and 113 of these tumor scans were positive. See the following publication in this regard:

III. Sparr, J. L.; Bale, W. F.; Marrock, D. D.; Dewey, W. O.; McCardle, R. J.; Harper, P. V.; "Labelled Antibodies to Human Fibrinogen. Diagnostic Studies and Therapeutic Trails", *Cancer,* 20: 865–870, 1967.

The lack of a direct association with the neoplastic process and the lack of specificity for any one neoplasm are the failings of the use of a fibrin antibody. Attempts to use rabbit antiglioma antibody by intracarotid infusion of radiolabelled immunoglobulin were associated with limited success, and the specificity of the antiserum was questionable.

Goldenberg, et al. published the successful results of their initial clinical trail of tumor detection and localization by scintillation scanning of patients injected with $I^{131}$-labelled heterologous(goat) antibodies to human carcinoembryonic antigen (CEA). See the following publications in this regard:

IV. Goldenber, D. M.: "Oncofetal and other Tumor-associated Antigens of the Human Digestive System", *Curr. Top. Pathol.* 63: 289–342, 1976.

V. Goldenberg, D. M.; Deland, F,; Kim, E. E.: "Human Chorionic Gonadotrophin Radioantibodies in the Radioimmunodetection of Cancer and the Disclosure of Occult Metastases" *Proc. Nat'l. Acad. Sci.* 78: 7754–7758, 1981.

VI. Goldenberg, D. M.; Deland, F.; Kim, E. E., et al.: "Use of Radiolabelled Antibodies to Carcinoembryonic Antigen for the Detection and Localization of Diverse Cancers by External Photoscanning", *N. Engl. J. Med.* 298: 1384–1388, 1978.

Tumor location could be demonstrated at 48 hours after the $I^{131}$-anti-CEA injection in almost all patients. See the following publications in this regard:

VII. Goldenberg, D. M.; Preston, D. F.; Primus, F. J.; Hansen, H. J.: "Photoscan Localization of GW-39 Tumors in Hamsters Using Radiolabelled Anticarcinoembryonic Antigen Immunoglobulin" *J. Cancer Res.* 34: 1–9, 1974.

VIII. Goldenberg, D. M.; Sharkey, R. M.; Primus, F. J.: "Carcinoembryonic Antigen in Histopathology: Immunoperoxidase Staining of Conventional Tissue Sections", *J. Natl. Cancer Inst.* 57: 11–22, 1976.

Of particular importance in connection with this investigation, ordinary scintigrams proved difficult to interpret because of blood-pool background radioactvity. Computer subtraction of radioactive blood-pool agents from the $I^{131}$-labelled heterologous (rabbit) antibody to human CEA was attempted to enhance imaging.

The noted carcinoembryonic antigen (CEA) is a tumor-associated antigen of gastrointestinal cancer and was first described by Gold et al. in 1965. See the following publication in this regard:

IX. Gold, P., Freedman, S. O.: "Demonstration of Tumor Specific Antigen in Human Colonic Carcinomata by Immunologic Tolerance and Absorption Techniques", *J. Exp. Med.* 121: 439–462, 1965.

The carcinoembryonic antigen, so named because of its noted presence in neoplastic and embryonic gastrointestinal tissues, has been characterized as a protein-polysaccharide complex. Clinical experience with CEA has shown that, while its marker function may also be present in non-malignant disease states, an increase in CEA levels with colon and pancreatic tumors is well established and serial CEA determinations have become a highly useful diagnostic tool. See the following publication in this regard:

X. Dhar, P.; Moore, T.; Zamcheck, N.: "Carcinoembryonic Antigen (CEA) in Colonic Cancer. Use in Pre-operative and Post-operative Diagnosis and Prognosis" *JAMA* 221: 31–35, 1972.

Investigations have shown that a high correlation exists between the level of circulating CEA and the extent of tumor. After resection presumed to be curative, CEA levels may fall or become undetectable; as tumor recurs, the CEA levels rise. A new low CEA level (baseline) is reached 7 to 30 days post-operatively, and any significant rise above this indicates tumor recurrence or progression. See the following publications in this regard:

XI. Joyce, S.; Lobe, T.; Martin, E. W. Jr.: "Direct Carcinoembryonic Antigen Assay in Diagnosis and Prognosis", *Surgery* 86: 627, 1979.

XII. Herrera, M. D.; Chu, T. M.; Holyoke, E. D.: "Carcinoembryonic Antigen (CEA) as a Prognostic and Monitoring Test in Clinically Complete Resection in Colorectal Carcinoma", *Ann. Surg.* 183: 5-9, 1976.

The use of radionuclide labelling of antibodies in conjunction with radio-detection equipment has continued to be the subject of development and study. In the recent past, advances in the technique are evidenced by the pursuit of the use of monoclonal antibodies or fragments thereof with a variety of radionuclides. Several techniques for imaging these antibodies are in use, for example tomographic scanning, immunoscintigraphy, and the like. The particular choice of radionuclide for labelling antibodies is dependent upon its nuclear properties, the physical half-life, the detection instruments's capabilities, the pharmacokinetics of the radiolabelled antibody, and the degree of difficulty of the labelling procedure. Generally, there are trade-offs of advantages and disadvantages with the election of any given radionuclide. The most widely used of these radionuclides in nuclear medicine imaging include Technetium $Tc^{99m}$, Iodine $I^{123}$, $I^{131}$, and Indium $In^{111}$.

For the most part, the endeavors to the present time in using antibodies to localize tumors of the gastrointestinal tract use the radionuclide $I^{131}$ as the marker or label. See publication VI above and the following publications:

XIII. Halsal, A. K.; Fairweather, D. S.; Bradwell, A. R. et al: "Localization of Malignant Germ-Cell Tumors by External Scanning After Injection of Radiolabelled Anti-Alpha-Feto-protein" *Br Med J.* 283: 942-944, 1981.

XIV. Sullivan, D. C.; Silva, J. S.; Cox, C. E. et al: "Localization of I-131 Labelled Goat and Primate Anti-Carcinoembryonic Antigen (CEA) Antibodies in Patients with Cancer" *Invest Radiol* 17: 350-355, 1982.

In spite of its somewhat extensive utilization, $I^{131}$ is not an ideal radionuclide for use in diagnostic medicine. The high energy gamma-photon emitted from $I^{131}$ is poorly detected by current instrumentation. In addition, the particulate emissions of $I^{131}$ deliver a high radiation dose to the patient. Other radionuclides of iodine have been considered not to be ideal for gamma camera or the like imaging of the biodistribution of radiolabelled antibodies because of the short physical half-life (27-35 kev) ($I^{123}$:13.2 hours) (27-35 kev) or very low energy gamma emission as will be evidenced with the use of $I^{125}$.

In effect, the external imaging techniques for detecting cancerous tumors using radiolabelled antibodies (e.g. to CEA) have been of minimal value to the surgeon. As a consequence, the surgical approaches in use resort to the dated procedures of vision and touch (palpation) in combination with locally determined protocols dictating the extent of tissue resection.

Tissue removed by resection during surgery includes not only tissue suspected by the surgeon of being neoplastic, but also includes an amount of healthy tissue taken because the precise tumor margins cannot be ascertained by the surgeon. Coupled with the devastating risk of not removing neoplastic tissue resulting in tumor recurrence, surgical protocol dictates that healty tissue be taken in order to ensure the removal of neoplastic tissue. Of course, the final determination as to whether the resected tissue is malignant falls to the pathologist who receives the tissue removed during the surgical procedure. Often, the pathologist will subject the tissue to immediate clinical observation and palpation in order to select a suitable site for more extensive tests to be conducted, e.g. a frozen section test. Often, the surgeon awaits the pathologist's decision before proceeding with a complete resection. Even following surgery, the pathologist's report is extremely important in confirming post-operative treatment of the patient. Too, the surgeon often looks to the pathologist to confirm that the margins of tissue removed are free of neoplastic tissue.

BROAD STATEMENT OF THE INVENTION

To achieve improved success in conjunction with this form of surgical treatment, a reliable and reproduceable technique for tumor isolation and differentiation is needed. The present invention is addressed to a method for the improved localization, differentiation, and removal of neoplastic tissue in animals. In particular, one aspect of the present invention involves a surgical procedure wherein an animal suspected of containing neoplastic tissue is surgically accessed and the tissue therein examined visually and by palpation for evidence of neoplastic tissue. The improved methodoloy commences with the administering to the animal of an effective amount of a labelled antibody specific for neoplastic tissue and labelled with a radioactive isotope exhibiting specific photon emissions of energy levels. Next, and importantly, the surgial procedure is delayed for a time interval following said administering for permitting the labelled antibody to preferentially concentrate in any neoplastic tissue present in the animal so as to increase the ratio of photon emissions from neoplastic tissue to background photon emissions in said animal. Thereafter, an operative field of the animal is surgically accessed and tissue within the operative field to be examined for neoplastic tissue has the background photon emission count determined. Once the background photon emission account for tissue within the operative field has been determined, a hand-held probe is manually positioned within the operative field adjacent tissue suspected of being neoplastic. The probe is configured for fascilé hand positioning and maneuvering within the operative field of the animal. The probe is characterized by having a collimatable radiation detector having a selective photon entrance and having an output deriving discrete signals responsive to photon emissions when said entrance is positioned immediately adjacent thereto. The probe further comprises amplifier means having an input coupled with said radiation detector output and responsive to said discrete signals to provide corresponding amplified output pulses. Finally, the probe comprises readout means responsive to said output pulses and actuable to an initial condition for commencing the provision of a perceptible indication of an indicia corresponding to the number of said output pulses received.

From the perceptible indication, the extent of tissue exhibiting a number of output pulses having a value above background output pulses is determined and such determined tissue removed surgically. Thereafter, the probe is manually positioned adjacent tissue surrounding the surgically removed tissue to determined from said perceptible indication whether any of said surrounding tissue still exhibits a number of output pulses having a value above said background output pulses. Any adjacent tissue surrounding the initial surgically removed tissue which does exhibit an increased number of output pulses is surgically removed additionally. Thereafter, the margins again are examined with the probe in order to ensure that all tissue exhibiting a number of output pulses having a value above the background output pulses has been removed.

Another aspect of the present invention permits the administering to an animal of an effective amount of a labelled antibody specific for neoplastic tissue which antibody is labelled with a radioactive isotope exhibiting photon emissions of select energy levels. If the foregoing novel methodology is to be employed during this improved procedure, then surgery is delayed as described above prior to surgically accessing an operative field of the animal. If only conventional visual and palpation protocol is to be practiced, then no delay of surgery following the labelled antibody administering is required.

This procedure then involves the surgical removing of tissue determined to be neoplastic. Such determination can be made by any procedure including visual inspection, palpation, and the foregoing improved methodology involving the hand-held probe. Regardless of the particular protocol employed in determining the tissue to be removed, the tissue removed from the animal during surgery then is subjected to the same procedure as is described above with respect to the surgical use of the hand-held probe. That is, the clinical setting has the background photon emission count determined initially followed by the positioning of the probe adjacent to the surgically removed tissue. From the perceptible indication, the extent of tissue exhibiting the number of output pulses having a value above said background output pulses is determined. Since extremely little background photon emission count ordinarily will be experienced, the ex vivo tissue can be quite accurately and reliably determined to be neoplastic or non-neoplastic and precise tumor margins accurately determined. This information will enable further tests to confirm the presence of neoplastic tissue, e.g. frozen section, to be determined readily. This information can be quickly communicated to the surgeon so that the surgical decision process can accommodate the ex vivo tissue results. Conveniently, such ex vivo determination is conducted by a pathologist with this method being an adjunct to conventional pathology procedures. For present purposes, ex vivo tissue is tissue from a patient who has had a labelled antibody administered thereto, and the tissue removed for neoplastic tissue determination by the probe.

Advantages of the present invention include the availability of an additional tool for the surgeon to utilize in the diagnosis and treatment of cancer. Another advantage is a method which accurately and reliably determines tumor margins so that all of the diseased tissue is removed and virtually no healty tissue is removed during surgery. Yet another advantage of the ex vivo procedure is that it enables more information to be reliably gathered and inputted to the surgeon which may alter the course of the surgical procedure and the post-surgical treatment of the patient. A further advantage is that the novel surgical procedures can be readily practiced by the skilled surgeon and implemented into conventional surgical surroundings. Yet another advantage is the ability to locate sub-clinical masses during surgery which sub-clinical masses heretofore could not be reliably determined by the surgeon. These and other advantages will be readily apparent to those skilled in the art based upon the disclosure contained herein.

Figure 1:
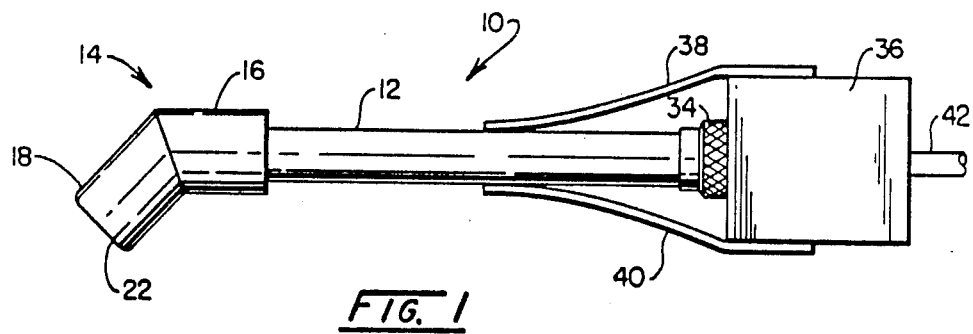
FIG. 1 is a plan view of one early model of a probe useful in accordance with the present invention.

The drawings will be described in detail below.

DETAILED DESCRIPTION OF THE INVENTION

As noted above, conventional surgical protocol during cancer procedures involves two main senses of the surgeon: sight and feel(palpation). In other words, the experience and skill of the surgeon utilizing his eyesight, his hands, and his experience are utilized in order to determine neoplastic tissue both for sampling for pathological confirmation and for resection of the malignant tissue. Two problems pervading cancer surgery involve the precise determination of the tumor margins (i.e. at what point does the neoplastic tissue cease and healthy tissue commence) so that large masses of healthy tissue are not unnecessarily removed along with the neoplastic tissue, and sub-clinical masses, i.e. those neoplastic tissue masses which are hidden from the sight and feel of the surgeon or are so small that they cannot be visualized or felt by the surgeon. Both of these problems add to the difficulties encountered by the skilled surgeon during cancer surgery. Finally, the final arbiter as to whether neoplastic tissue has been found is the pathologist. The pathologist confirms to the surgeon that the margins of the resected area are free of neoplastic tissue (i.e. all of the neoplastic tissue has effectively been removed) and that the tissue selected by the surgeon for sampling indeed is malignant (i.e. cancerous). The pathologist also relies on sight, feel, and experience in order to determine precisely where the frozen section sample is to be taken. While the entire sample is subject to pathological histochemical analysis following the surgery, such procedure often takes several days. What the surgeon needs and what the pathologist strives to provide is confirmation of neoplastic tissue while the patient still is in the operating room. If the pathologist fails to suitably select a site for immunohistochemical analysis, then the surgeon may not remove neoplastic tissue. Thus, morbidity and prognosis of cancer patients indeed would be radically improved by improving the surgical and pathology protocols involved in cancer surgery.

The invention brings a new sense to the forefront in cancer surgery: sound. Now the surgeon and the pathologist can "hear" neoplastic tissue in addition to utilizing the sense of sight and sense of touch. Of course, by "hear" is meant to include a perceptible indication to the surgeon or pathologist that neoplastic tissue has been located and differentiated from healty tissue. Since the surgeon and the pathologist are required to utilize their sense of sight and sense of touch in order to locate neoplastic tissue, it would be inappropriate for the surgeon or the pathologist to continually look up in order to locate a visual display which would indicate neoplastic tissue. Thus, the inventive methodology preferably operates on the surgeon's and pathologist's sense of sound as a new sense which can aid in the location and differentiation of neoplastic tissue.

Accordingly, the purpose of the present invention is to add to the arsenal of weapons that medicine has at its disposal in the surgical management of cancer and other disease processes, and not the replacement of traditional protocol involving sight and palpation. The present invention includes surgical methodology and pathology methodology, and a new relationship between the surgeon and the pathologist in making surgical decisions during cancer surgery. As the invention is cumulative in cancer management, conventional diagnostic evaluation still can be employed. Such conventional diagnostic evaluation, for example, of patients with primary disease include barium enema, computerized axial tomography, serum CEA assay, and colonoscopy. Patients with suspected recurrent colorectal disease can involve diagnostic evaluation including, for example, a CAT scan, hepatic arteriogram, and magnetic resonance imaging, when indicated. Further, chest X-rays, bone scans, liver scans, spleen scans, and like conventional diagnostic evaluation still is appropriate as the case admits.

As alluded to above, the new surgical methodology commences with the use of labelled antibodies or antibody fragments specific for neoplastic tissue. It is believed that the present invention is the first successful use of radiolabelled antibodies for the diagnosis and for the treatment of cancer. Referring to the label, initial investigation and studies were carried out utilizing Iodine 131 ($I^{131}$) as the labeling isotope. The utilization of this isotope stemmed from its traditional use in conjunction with external imaging devices. This isotope has an 8.07 day half-life and 79% of it will exhibit photo energy levels of 365 kev, 6.7% of the isotope exhibits a 673 kev energy level, 5.9% of the isotope exhibits a 284 kev energy level; 2.6% of the isotope exhibits an 80 kev energy level, and 1.8% exhibits a 723 kev level. As is apparent, this is a relatively highly energetic isotope and its selection during early investigational studies on the present invention stems from the prior energy requirements of the external scanning devices. Refinement of the surgical and pathology methodologies of the present invention enable the use of $I^{131}$ to continue, though its short half-like and high energy gamma radiation emissions make it not as suitable as other isotopes. With respect to the latter condition, it will be observed that the immediate adjacency between the selective photon entrance of the probe and the organ being examined make it more difficult to configure a collimatable radiation detector of suitable size for intra-operative use which still will capture sufficient gamma radiation emissions for detection of the neoplastic tissue. Accordingly, more recent studies utilizing the improved inventive methodology focused on lower level energy isotopes exhibiting photon emissions of energy levels less than about 300 kev advantageously and preferbly less than about 150 kev. Thus, utilization of Indium 111 ($In^{111}$), Iodine 125 ($I^{125}$), Selenium 75 ($Se^{75}$), or Cobalt 57 ($CO^{57}$) are examples of lower energy level isotopes which may be suitable for utilization in labelling antibodies specific for neoplastic tissue. Presently, $I^{125}$ is the isotope of choice since it exhibits a suitably long half life (60 days) and possesses an energy level which makes design of a collimatable radiation detector of suitable small intra-operative size quite practical. Labelling procedures have been well documented and discussed in the literature so that such procedure is easily practiced by those skilled in the nuclear medicine art.

The dosage of labelled antibody is such that the handheld probe can be utilized for the effective localization and differentiation of neoplastic tissue from healthy tissue. Such dosages can be as small as 1 millicuries of isotope per milligram of antibody, though the dosage can range up to about 5 millicuries of label per milligram of antibody. Of course, the specific type of label, type of antibody, and like factors may affect dosage requirements as those skilled in this art will appreciate.

Referring now to the antibodies specific for neoplastic tissue, it will be observed that a myriad of antibodies have been generated over the past decade or so, yet governmental approval of antibodies for in vivo human use in cancer diagnosis and treatment is a goal yet to be achieved. Suitable antibodies specific for neoplastic tissue for present purposes include whole polyclonal antibodies, whole monoclonal antibodies, antibody fragments, and the like and mixtures thereof. Of course, development of suitable specific antibodies to different types of cancer may have a profound impact upon the methodology of the present invention. Suitable specific antibodies confirmed in human studies employing the methodology of the present invention include CEA antibodies (antibodies to carcinoembryonic antigen); monoclonal antibody 17-1A and its F(ab')$_2$ fragment (Wistar Institute, Philadelphia, Pa.); monoclonal antibody 19-9 and its F(ab')$_2$ fragment (Centocor, Inc., Philadelphia, Pa.); and monoclonal antibody B72.3 (Dr. Jeffrey Schlom, National Cancer Institute). The human trail data in this application will provide ample evidence of the efficacy of such specific antibodies for labelling and use in the surgical and pathology methodologies of the present invention. It will be appreciated that a variety of additional antibodies likewise will find acceptance and efficacy in accordance with the precepts of the methodology of the present invention.

As the human trial data will confirm, the presence of some labelled antibodies in neoplastic tissue is evidenced up to 40 days following injection. Further, such labelled antibody also is quite detectable utilizing the probes disclosed herein. This means that the progress of treatment of cancer (chemotherapy, radiation treatment, or the like) can be followed in order to determine the efficacy of such treatment. Of course, such longer term detection of the labelled antibodies was specific to whole monoclonal antibodies, though polyclonal antibodies may exhibit such duration additionally. Antibody fragments, however, tend to be bound to the cancer sites for only a matter of a few days, so that their use necessitates more immediacy in the surgical methodology of the present invention. It currently is believed that mixtures or cocktails of antibodies may ultimately provide the broadest spectrum of effectiveness in accordance with the methodology of the present invention.

After the effective amount of the labelled antibody has been administered to the patient (animal including human), surgery is delayed for a time interval following administering for permitting the labelled antibody to preferentially concentrate in neoplastic tissue and to be excreted from the remaining healthy body tissue of the animal. This increases the ratio of photon emissions from neoplastic tissue to background photon emissions. The detection of neoplastic tissue necessarily is a comparative function wherein gamma radiation emissions between two tissue sites are compared so as to determine a ratio. Background radiation existing in the operating room as well as in the body of the patient always will be present and must be taken into account when locating and differentiating neoplastic tissue thereby.

Conventional nuclear medicine literature teaches that a time period of between about 24 to 96 hours following administering of the labelled antibody should be practiced for radio-immuno detection utilizing conventional external scanning instruments. Accordingly, early studies conducted in accordance with the instant methodology likewise followed the 2-4 day time interval during which surgery was delayed. Even with the most sensitive detection instrument and the preferred $I^{125}$-labelled monoclonal antibody, tumor-to-background ratios were detectable, though not overy evident. The blood pool background existing in the patient, especially the liver, made the locating and differentiation of neoplastic tissue somewhat rely upon subjective analysis of the data, i.e. the sound emitted as a perceptible indication of an indicia corresponding with the number of output pulses detected by the probe. In order for the instant methodology to be truly of benefit in cancer management, it was felt that subjective interpretation should be minimized as much as possible so that the determination of neoplastic tissue was not dependent upon observer interpretation.

Quite dramatically and unexpectedly, it was discovered that surgery could be delayed for a much longer interval of time and that such additional time period results in the blood pool background radiation in the patient being brought down to about that background which exists in the operating room naturally. While such time period during which surgery is delayed is dependent upon antibody type, half-life of the label, and the ability of the patient to accommodate the extra delay, it has been found that surgery advantageously can be delayed for a time period of at least about 7-10 days, and often 14-21 days. Regardless of how the body metabolizes the unbound labelled antibody, such longer time interval of delay following administering of the labelled antibody enables a probe to be designed which can window out the low background counts and correspondingly respond, i.e. emit sound, only when neoplastic tissue has been located and differentiated. Now, the detection and differentiation of neoplastic tissue is not dependent upon observer interpretation which makes a truly revolutionary and useful methodology in the management and treatment of cancer.

As noted above, the time delay when utilizing antibody fragments is not nearly as long as when polyclonal and monoclonal antibodies are utilized, yet the unexpected discovery of the significance of this time interval, once known, enables the skilled surgeon to evaluate various labelled antibodies in order to determine the optimum time period during which surgery should be delayed. Indeed, with the unexpected discovery that such labelled antibodies can be detected for time periods of 30-40 days following their being administered to the patient, truly brings a needed degree objectivity to cancer surgery. Even in the liver, the main blood pool background in the abdomen, neoplastic tissue can be quite readily located and differentiated when the extra time interval is employed prior to surgery. On this subject, it also should be understood that a "hot" spot in the abdomen is in the stomach whereat hydrochloric acid is produced. Apparently, halogen interchange occurs which enables the probe to detect a "hot" spot in the stomach ordinarily interpretable as neoplastic tissue.

This hot spot location is a problem when external imaging of the patient is practiced. The surgeon can visualize and palpate this location to determine the presence or absence of neoplastic tissue (to the extent that any neoplastic tissue present can be detected by the surgeon by vision or palpation). Conventional chemical blockers can be utilized in order to mask this source of labelled antibody during surgery. These same comments hold true for the thyroid which naturally takes up iodine circulating in the system.

The next step of the methodology involves the in vivo utilization of a hand-held probe within the operative field wherein such probe is manually placed adjacent tissue suspected of being neoplastic. The probe is configured for fascile hand positioning and maneuvering within the operative field of the patient. The fact that the probe may be directed from any angle and may be brought very close to the tissue being examined is important in overcoming the inverse square law that governs the intensity of radiation from a small source, e.g. sub-clinical masses. Since the probe is being utilized in vivo within the patient's body, it necessarily must be quite small and have a comfortable feel for the surgeon. The probe is characterized by having a collimatable radiation detector having a selective photon entrance. Collimation utilizing a lead or other collimator enables the surgeon to initially scan a broad area of tissue in order to detect gamma radiation and then collimate the radiation detector so that only a very narrow field is being viewed for precise location and differentiation of neoplastic tissue.

By positioning the sensing head of the probe in immediate adjacency with the organ carrying the possible tumor, all of the potential disadvantages occasioned by the inverse square law of radiation propagation are avoided. The probe must be useable within the body cavity and thus must be sterilizable (e.g. gas sterilization, autoclaving, use of a sterilized thin bag to house the probe, etc.) and must be configured such that the surgeon can readily manipulate it about various organs of the body cavity. To achieve a requisite small, hand manipular size, a radiation detecting arrangement was developed which may be adequately shielded and which may trap sufficient photons to achieve requisite sensitivity. In this regard, germanium devices are unacceptable inasmuch as their operational temperature ranges are at cryogenic levels. Similarly, silicon devices require a size which was considered unacceptable for the instant application. To achieve the requisite smallness while maintaining a high photon stopping power for the gamma radiation anticipated, a cadmium telluride detector, having an adequately high atomic number and, thus, high stopping power, was provided. The high stopping power and low leakage which occur during performance at room temperature, appeared ideal for the instant application, however, the cadmium telluride detectors do exhibit deep traps for electrons produced by gamma radiation and these traps load slowly such that the characteristis of the diodes will change with time, ie. exhibit a drift in sensitivity. In connection with the above commentary, reference is made to the following publication:

XVII. Siffert, P.: "Current Possibilities and Limitations of Cadmium Telluride Detectors", *Nuc. Inst. & Methods* 150: 1-12, 1978.

Improvements in the drift in sensitivity for the cadmium telluride detectors has been achieved, for example, through resort to improved contacts, for example using platinum. In this regard, see the following publications:

XVIII. Serreze, H. B.; Entine, G.; Bell, R. O.; and Wald, F. V.: "Advances in CdTe Gamma-Ray Detectors" *Trans. in Nuclear Science,* Vol. NS21, No. 1, pp 404–407 (Feb., 1974).

Where the use of a cadmium telluride detector is preferred, it will be appreciated that a sodium iodide crystal-type detector additionally may find use in accordance with the present invention, though size of such scintillation detector must be taken into account. With respect to the cadmium telluride detector, it has been determined that utilization of an array of crystal enables a "camera" probe to be developed which can have a visual display associated with it whereby the neoplastic tissue is visually imaged on the probe for the surgeon to easily view during scanning of the tissue. Gross determination of neoplastic tissue may be enhanced by utilization of such technique followed by use of a more precise and smaller version of the probe wherein precise tumor margins can be located and differentiated from healthy tissue. Though such camera probe may have a visual readout, an additional perceptible indication involving sound likewise has been determined to be quite useful as an adjunct thereto. The sense of sound has been determined to be readily acceptable and of value to the surgeon as a perceptible indication of an indicia corresponding to the number of output pulses received by the probe during surgery.

A sequence of hand-manipular probes were evolved leading to the currently favored probe. The initial models of the probe utilized a block of CdTe crystal nominally 2.8 by 2.8 mm and 2 mm in thickness. The initial collimator utilized was of nickel material and had about a 2 inch diameter. A coaxial cable from the preamplifier associated with the detector crystal connected the model 1 probe to a control unit which converted the signals received to an audible output. The model 2 probe utilized a lead collimator in place of the nickel collimator due to the initial utilization of $I^{131}$ as the label for the antibody. Model 3 was like model 2 but a protective conduit was used to protect the coaxial cable and shield it from the environment.

Figure 2:
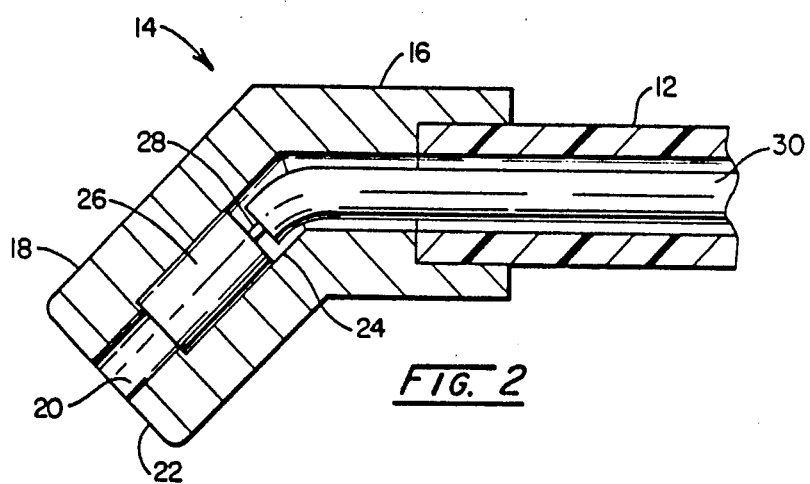
FIG. 2 is an enlarged sectional view of the tetra-collimator region of the probe of FIG. 1.

FIGS. 1 and 2 show a view of probe model 3. Looking to FIG. 1 an intra-operative probe is shown at 10 which includes a tubular housing 12 which was fashioned from a rigid plastic material. At the tip of tubular housing 12 was fashioned a lead collimator represented generally at 14 which collimator was formed having a first portion 16 attached to the tip of housing 12 and which has a generally cylindrical shape, the axis of which is parallel with the contral axis of housing 12. Collimator 14 additionally includes a second cylindrical shaped portion 18, the centrally disposed axis of which is oriented at an angle of about 45° with the noted axis of portion 16.

Looking additionally to FIG. 2, it may be seen that forward portion 18 of collimator 14 includes an entrance aperture tunnel 20 having walls which are cylindrically shaped and extend from the forward face 22 of forward portion 18 to a stepped counter-bore 24. Counter-bore 24 is formed having a diameter suited for receiving cylindrically shaped cadmium telluride detector 26. The output leads from detector 26 at 28 are coupled to grounded coaxial shielded cable 30 which extends through tubular housing 12. Returning to FIG. 1, cable 30 is coupled through high quality coaxial cable connector 34, for example A, B, and C connector, to preamplifier 36. The connections of coaxial cable 30 with detector 26 are quite delicate, thus rigid plastic housing 12 serves to support cable 30 from bending torques and the like occasioned in use, as well as providing one form of handle for the surgeon. To further stiffen housing 12, straps, as at 38 and 40, have been secured between housing 12 and the housing of preamplifier 36. Coaxial cables, as at 30, of course, exhibit a capacitance from the shield to the inner conductor and the charge generated by diode detector 26 is called upon to charge up this capacitance.

The 45° angular orientation of collimator portion 18 serves the dual function of permitting the surgeon to manipulate probe 10 beneath organs within the body cavity as well as to block radiation which may be background or the like which would be otherwise impinging toward the rearwardly disposed side of detector 26. By orienting detector 26 within the forward portion of collimator 14, as shown in FIG. 2, this radiation effectively is avoided. Model 4 of the probe utilized a 45° angle between the handle of the probe and the collimator and employed a stainless steel housing for the probe of about 8 inches in length. The angled collimator with respect to the handle was a surgically-requested design feature which permitted easier access to various of the organs within the abdomen.

The model 5 probe was made of nickel and had a tapered collimator set at a 45° angle from the handle and was specifically designed for use with $I^{125}$. Model 6 employed a removable collimator and utilized plastic braces to support the coaxial cable fitting to the handle of the probe. Brass supports on model 7 replaced the plastic braces on model 6.

The model 8 probe was the first version to utilize a much larger CdTe crystal, measuring about 10 mm square and 2 mm thick. The model 9 version of the probe employed a plastic shrink wrap surmounting the stainless steel body. A collimator angle with respect to the handle of 30° finally was arrived at as being the most convenient for the surgeon to utilize.

The probe desirably is sterilizable, either by gas or heat (autoclave), and is designed to be battery powered for convenience and safety. The control unit connected to the probe via a coaxial cable is designed to be located outside of the surgical field. The currently preferred probe of Denen et al. (cited above) utilizes a collimator about 1¼ inch in length affixed to a handle which measures about 6 inches in length. The noted 30° angle with respect to the collimator and handle is maintained. The cadmium telluride crystal is located about 5–6 mm behind the collimator and the total weight of the probe is about one-half pound. The housing of the probe is constructed from solid copper and the exterior is nickel plated. The copper housing provides additional shielding for the preamplifier located within the housing.

Prior cadmium telluride probes, such as marketed by Radiation Monitoring Devices, Inc., Watertown, Mass., publish one beep per gamma ray detected by the probe. With such an audible output, it is extremely difficult to distinguish between background and source radiation, especially at the relatively low counts which can be seen in the inter-operative process of the present invention, e.g. as low as about 5–10 counts per second. Thus, the Denen et al. probe provides an audible output which can be selected from beeps, clicks, and a siren, depending upon the particular use of the probe and surgical preference. The audible output is based on a microprocessor continuously monitoring the number of pulses detected by the cadmium telluride detector and such processing is done in real time. On the siren selectable audible output mode, an octave increase in the sound for every doubling of the number of counts detected provides a most effective aubidle indicia for the surgeon and has been met with great success by surgeons utilizing the probe in accordance with the surgical methodology of the present invention.

While the probe is specifically designed to utilize $I^{125}$ which isotope was chose for its long half life, the ability to utilize more accurate isotopes or even combinations of isotopes is rendered practical by two factors. The first factor is the ability to delay surgery for an extremely long time, thus permitting the body to rid itself of the labeled antibody not bound to a tumor site, and the development of a probe sensitive enough to still pick-up radioactivity at the tumor site. The second factor is a threshold control designed in the control unit affixed to the probe whereby an upper and a lower energy threshold limit can be set. Thus, such windowing out feature permits, for example, background to be determined and a lower threshold set just above background. Under such a threshold setting with background radiation being windowed out, the probe only will pick-up tumor sites. Next, the upper threshold limit can be set so as to exclude extraneous sources of radiation (e.g. cosmic radiation), or can window out a higher energy source such as $I^{131}$, thus permitting a combination of isotopes to be injected into the patient.

Additional design features which the preferred probe exhibits are its publication of battery strength, count time, number of counts detected, indication of recharging mode for the batteries, noise level, pulse height of the signals detected, and threshold selections. The perceptible indication, while desirably sound, could be light, a chart, or the like. Thus, it will be observed that a uniquely sophisticated and designed probe has evolved.

Accordingly, suitable probes for utilization in accordance with the present invention involve the real time, instantaneous generation of a perceptible indication (desirably sound) of an indicia corresponding to the number of output pulses received by the probe. Further, an adjustable threshold enables the probe to only respond in the presence of neoplastic tissue and by suitable manipulation of the threshold, the surgeon can narrow in on a peak for localization of the neoplastic tissue. Finally, employment of an audible indicia wherein the sound increases an actave in pitch for every doubling of the number of counts, or similar technique, makes for an instrument which has a substantial impact on the surgeon and contributes to the objective location of neoplastic tissue wherein subjective interpretation has been virtually eliminated.

The probe is utilized in vivo during a surgical procedure wherein an operative field is addressed by the surgeon. A variety of organs containing neoplastic tissue have been successfully treated by the surgical methodology of the present invention including, for example, breast, ovaries, pancreas, gastro-intestinal tract, and colon. In fact, the probe has enabled the surgeon to externally scan the perineal area in order to confirm neoplastic tissue which then permits the surgeon to perform a less extensive surgical procedure by accessing the perineal areas as the operative field rather than accessing such area via the abdomen. Successful procedures are reported in the data wherein patients have been able to be discharged from the hospital in as short as two days following such limited surgical procedure. Such is the impact which the methodology of the present invention has on the surgical management of cancer. Further, such methodology is useful in primary cancer cases as well as in second-look surgeries.

The methodology involves the utilization of the probe in order to determine samples which can be sent to pathology for frozen section and other histochemical analysis, to determine margins for the surgeon to resect the diseased area, and in the determination of sub-clinical masses. The surgeon merely maps out the area determined by sight, palpation, and the probe, and then performs conventional resection of such tissue. Thereafter, the probe again is placed adjacent the suture lines in order to ensure that the margins are free of disease. Also, the inventive methodology has proved extremely useful in determining secondary occurrences of cancer, such as skip lesions and the like which may be overlooked by the surgeon. Following resection, additional tissue may need to be removed in order for the entire maring of the resected area to be "soundless" or free of tumor.

In addition to the in vivo aspects of the improved methodology, ex vivo examination of tissue with the probe additionally is a further aspect. The surgeon in the operating room may employ the probe to examine excised tissue ex vivo or a pathologist may utilize the probe to examine the removed tissue ex vivo. The sensitivity of the probe in detecting neoplastic tissue is increased since the blood pool background in the patient has been totally removed. Cancer sites containing as few as 3,900 cells (about 0.1 cubic millimeter) have been determined ex vivo. In this regard, cancer sites containing as few as $6.25 \times 10^5$ cells (less than 1 cubic millimeter) have been determined in vivo. Accordingly, the probe signals can be used to select tissue in vivo to be sent to the pathologist for frozen section examination. Ex vivo counting and immunohistochemical staining of pathologic material are needed to evaluate the specificity of the inter-operative probe data. The results of ex vivo probe counting by the pathologist also aids in tumor staging by detecting metastatic disease which cannot be seen or palpated. It will be appreciated that pathological determination of diseased tissue during surgery involves mircoscopic examination of tissue which means that the situs of the tissue specimens selected by the pathologist is of critical importance. Ex vivo use of the probe in accordance with the pathology methodology of the present invention enables the pathologist to more accurately select appropriate tissue for immunohistochemical staining. Thus, tumor margins and sub-clinical masses can be more accurately confirmed by the pathologist while the patient still is in the operating room. Thus, a new concept in the surgical management of cancer patients which changes and enlarges the traditional intra-operative consulting role between the pathologist and the surgeon has been revealed.

Ex vivo probe counting can be performed during the surgical procedure with directed selection of positive tissue (by visualization, palpation, or probe positive determination) for frozen section evaluation by the surgical pathologist. This will allow for very sensitive and rapid selection of tissue samples to be evaluated by the pathologist for tumor spread. Results of the probe guided frozen section diagnosis will be communicated to the surgeon before the patient is closed. The detection of metastatic diseases near or at the margins of the resection and pattern of spread of the malignancy will allow the surgery to be altered or extended. Intra-operative consultation between pathologist and surgeon will define more precisely the extent of tumor.

As indicated earlier herein, the probe apparatus of the invention was evolved over a period of experimentation which included preliminary studies designed in conjunction with several sets of experiments serving to evaluate those factors important in tumor radioimmunodetection as they relate to the operation of such a small radiation detector. Of primary importance in this effort was the determination of the validity of specific baboon antisera and its recognition of the CEA antigen expressed in the CX-1:Tumor. In a first phase of study, the validity of the specific antibody-antigen recognition in enhancing radiolabelled antisera was confirmed. Radiolabelled CEA-specific baboon antisera was injected into nude mice bearing the CX-1:Tumor which is a known producer of CEA. It was also injected into nude mice bearing non-CEA producing human glioma tumor U-251. A non-specific antisera, alpha G 15-As, which recognizes human breast cyst fluid was also injected as a negative control. It was injected into the two tumor models mentioned above. The CEA-As and CX-1 model represented the only group injected with an antisera specific for a known tumor associated antigenic site. Varying degrees of localization werre noted in the non-specific groups (see Tables 1 through 4 below.) A cadmium telluride detector and type CTC-4 counter marketed by Radiation Monitoring Devices, Inc., Watertown, MA, was utilized in this study.

TABLE 1

GDPI$^{131}$-α-G15-As Activity in U-251 Tumor

| Hours Post Injection | Tumor Counts (Mean) | Opposite Flank Counts (Mean) | Ratio ± S.D. Tumor Counts Opposite Flank Counts | Log Ratio + S.D. |
|---|---|---|---|---|
| ½ | 1437 | 1562 | 0.936 ± 0.127 | −0.074 ± 0.129 |
| 24 | 705 | 587 | 1.193 ± 0.096 | 0.173 ± 0.082 |
| 48 | 510 | 364 | 1.374 ± 0.237 | 0.304 ± 0.176 |
| 72 | 410 | 278 | 1.457 ± 0.180 | 0.370 ± 0.121 |

TABLE 2

GDPI$^{131}$-CEA-As Activity in U-251 Tumor

| Hours Post Injection | Tumor Counts (Mean) | Opposite Flank Counts (Mean) | Ratio ± S.D. Tumor Counts Opposite Flank Counts | Log Ratio + S.D. |
|---|---|---|---|---|
| ½ | 1497 | 1543 | 0.974 ± 0.173 | −0.041 ± 0.185 |
| 24 | 240 | 200 | 1.182 ± 0.146 | 0.160 ± 0.120 |
| 48 | 134 | 56 | 1.272 ± 0.195 | 0.229 ± 0.156 |
| 72 | 92 | 71 | 1.320 ± 0.204 | 0.266 ± 0.157 |

TABLE 3

GDPI$^{131}$-α-G15-As Activity in CX-1 Tumor

| Hours Post Injection | Tumor Counts (Mean) | Opposite Flank Counts (Mean) | Ratio ± S.D. Tumor Counts Opposite Flank Counts | Log Ratio + S.D. |
|---|---|---|---|---|
| ½ | 764 | 731 | 1.069 ± 0.140 | 0.060 ± 0.133 |
| 24 | 272 | 253 | 1.086 ± 0.058 | 0.081 ± 0.052 |
| 48 | 193 | 176 | 1.110 ± 0.119 | 0.100 ± 0.108 |
| 72 | 141 | 130 | 1.100 ± 0.208 | 0.080 ± 0.181 |

TABLE 4

GDPI$^{131}$-CEA-As Activity in CX-1 Tumor

| Hours Post Injection | Tumor Counts (Mean) | Opposite Flank Counts (Mean) | Ratio ± S.D. Tumor Counts Opposite Flank Counts | Log Ratio + S.D. |
|---|---|---|---|---|
| ½ | 814 | 881 | 0.936 ± 0.139 | −0.076 ± 0.150 |
| 24 | 170 | 129 | 1.346 ± 0.313 | 0.274 ± 0.219 |
| 48 | 115 | 76 | 1.560 ± 0.290 | 0.428 ± 0.182 |
| 72 | 94 | 56 | 1.732 ± 0.355 | 0.530 ± 0.204 |

The above-noted localization was due to a variety of non-specific factors such as impaired tumor, blood and lymph flow, central avascular tumor necrosis and increased extra vascular extra-cellular space. These factors are all known to contribute to non-specific trapping of high molecular weight radiolabelled proteins. In no instance was the localization as great as in the CEA-As and CX-1 model (Table 4).

Enhanced localization of this specific antisera antigen model was attributed to the specific antigen-antibody recognition interaction and was statistically greater than the three non-specific antisera group (p 0.01).

As a second phase of the initial studies, four weeks following tumor implantation, four groups of mice were injected intraperitoneally with $I^{131}$ labelled baboon CEA antisera in four separate doses of 1, 5, 22 and 44 microcuries. An initially devised probe utilizing a cadmium telluride detector as above described was used to count radioactivity over the tumor, sacrum, and thyroid at ½, 24, 48 and 72 hours following injection. Preferential tumor location was detected by 24 hours in the mice injected with the 22 and 44 microcurie doses. Conventional gamma camera imaging was able to detect only a very faint tumor image. It was concluded from this that the small probe utilized had a greater sensitivity than external simulation cameras for tumor localization.

As a third phase of the preliminary studies, the performance of an earlier model of the probe of the invention with respect to radioactive isotope localization in tumors of various sizes was examined. A group of CX-1 tumor-bearing mice was injected with 40 microcuries of CEA antisera. The tumors in these mice had been implanted anywhere from 2 to 7 weeks before injection. A control group of mice without tumors was used for the 0 week group. The two-week old tumors were approximately 2 to 5 mm in size, and on cross-section on microscopic examination were composed entirely of viable tumor cells. The older tumors, which measured up to 23 mm in diameter, on cross-sectional microscopic examination, had approximately 60% central necrosis. Statistically, the 0 week tumor mice could be separated from the tumor-bearing mice at P 0.001. Also, the tumor localization index ratio as obtained immediately after and 24 hours following injection could be separated from the rest of the tumor counts. The ratios on days 3 and 4 in the mice with tumors from 2 to 7 weeks following implantation could not be separated. The ratios were independent of time from tumor transplant and tumor volume (P 0.35, F-test) (Table 5).

TABLE 5

Comparison To Tumor Isotop Localization in Relation To Time Since Xenografting

| GDP Reading Post-Antisera Injection (Hours) | Weeks Post Tumor Implanting (n)* | | | | | | |
|---|---|---|---|---|---|---|---|
| | 0 (4) | 2 (11) | 3 (10) | 4 (15) | 6 (4) | 7 (4) | Mean |
| ½ | 0.02954 | −0.25605 | −0.10216 | −0.01955 | −0.00303 | 0.11651 | −0.07615 |
| 24 | 0.01442 | 0.28871 | 0.27308 | 0.28844 | 0.34495 | 0.45342 | 0.28235 |
| 48 | −0.01260 | 0.54370 | 0.36719 | 0.44995 | 0.39673 | 0.43639 | 0.41764 |
| 72 | −0.05052 | 0.51254 | 0.39624 | 0.55193 | 0.40381 | 0.40985 | 0.44718 |
| Mean | −0.00479 | 0.27222 | 0.23359 | 0.31769 | 0.28561 | 0.35404 | 0.26776 |

*Represents number of mice in each group.

As a fourth phase of the investigation, varying doses of radiolabelled isotope were injected into mice with 3 to 4 week old tumors. Gamma well determined tissue activity expressed its percent dose per gram of tissue range from 0.13% to 2.77% with a median of 1.07%. Detectable radioactivity was higher in the tumor than in the normal adjacent tissue (muscle and skin) (See Table 6).

TABLE 6

Gamma Well Determined Organ Activity Counts Per Minute/Gram of Tissues
Mean ± S.D. (Minimum–Maximum)

| Injected Dosage (n)* | 40 Ci (25) | 100 Ci (4) | 140 Ci (5) | 20 Ci (11) |
|---|---|---|---|---|
| Blood | 85,421 ± 59,139 (10,228–193,268) | 128,488 ± 100,920 (36,000–257,358) | 320,984 ± 57,441 (270,771–401,462) | 442,611 ± 178,914 (131,200–671,660) |
| Heart | 24,664 ± 15,506 (7,345–62,355) | 39,196 ± 25,646 (13,869–63,654) | 108,217 ± 17,736 (90,076–131,690) | 155,295 ± 77,706 (33,440–296,061) |
| Liver | 46,720 ± 29,252 (7,772–109,385) | 80,942 ± 78,992 (202–173,873) | 186,793 ± 17,638 (155,526–197,415) | 326,037 ± 107,329 (60,610–452,148) |
| Spleen | 44,645 ± 34,175 (9,220–122,244) | 72,882 ± 55,420 (23,188–122,942) | 169,158 ± 62,964 (128,316–279,918) | 284,644 ± 111,440 (49,177–404,815) |
| Lung | 42,220 ± 29,250 (10,155–100,715) | 58,385 ± 35,868 (23,362–91,580) | 186,268 ± 101,328 (109,170–363,586) | 246,624 ± 132,201 (58,364–532,284) |
| Kidney | 36,851 ± 23,689 (10,834–87,448) | 96,955 ± 55,189 (47,506–153,682) | 142,838 ± 47,101 (103,123–221,204) | 218,970 ± 61,519 (62,559–290,959) |
| Intestine | 11,541 ± 8,242 (1,549–28,731) | 13,420 ± 9,032 (5,439–24,618) | 41,555 ± 19,695 (24,068–69,815) | 60,763 ± 28,287 (11,476–118,240) |
| Muscle | 24,566 ± 28,268 (5,377–149,260) | 23,020 ± 11,598 (12,742–38,876) | 108,162 ± 32,257 (84,520–163,925) | 211,081 ± 278,609 (27,300–861,000) |
| Skin | 39,438 ± 25,277 (8,450–98,960) | 58,654 ± 18,929 (31,998–74,685) | 146,270 ± 33,876 (114,342–196,928) | 218,168 ± 119,695 (61,462–486,433) |
| Tumor | 82,695 ± 58,768 (21,609–210,800) | 133,948 ± 91,348 (38,090–229,000) | 344,082 ± 68,042 (264,059–444,881) | 415,367 ± 294,476 (149,366–1,124,400) |
| Thyroid | 21,638 ± 12,998 (5,205–47,200) | 26,410 ± 15,286 (14,573–48,383) | 82,513 ± 24,850 (56,250–123,341) | 119,935 ± 58,720 (56,491–236,363) |

*Represents number of mice in each group.

As a fifth phase of the preliminary study, the validity of performance of the probe was examined by correlating the counts or output signals of the probe with gamma well tissue counts. Mice were sacrificed following the 72 hour reading and various organs were counted in a sodium iodide crystal gamma well. A linear relationship with the gamma detector probe measured activity was found (P 0.0001).

At the time of the sixth phase of the preliminary study, it was apparent that enhanced localization was evident in the tumor compared to the contralateral control site. Selected mice were imaged with an external gamma scintillation camera following the 40 microcurie injection. However, even imaging for as long as 60,000 counts, the investigators were unable to adequately image the tumor. This phase of the investigation involved the injection of escalating doses of radiolabelled isotope from 40 to 200 microcuries. Only when doses in the range of 150 to 250 microcuries were injected were the investigators able to successfully image the tumor xenograft with an external scintillation camera. This situation made apparent the sensitivity of the miniature probe in determining tumor localization as compared to conventional techniques of external scanning.

As a seventh phase of the preliminary investigation, the investigators were concerned the tumors located in the flank might be picking up increased activity from radioactive circulating immune complexes trapped in the liver reticulo-endothelial (RE) system. Thus, an investigation involving mice with tumor implants on the thigh which is a greater distance from liver radioactivity was carried out. Comparison of tumor localization ratios between the flank and thigh showed no statistical difference between these to anatomic sites. All studies from this point in time involve tumor xenografts located on the thigh.

In the above investigations, several polyclonal antibody sources were used fo tumor radioimmune detection. In particular, baboon antisera were utilized. In the eighth phase of the preliminary investigation, study was made involving comparisons of polyclonal antisera obtained from the goat (supplied by Primus) to the baboon antisera (supplied by Haagensen). Previous work had shown that both of these polyclonal antibodies are directed against protein antigenic determinants on the carcinoembryonic antigen. Tumor immunolocalization in the nude mice using both the miniature probe of the invention and gamma well counts were studied. 200 microcuries of iodine 131 antisera were injected intraperitoneally into CX-1 tumor bearing mice. Gamma radiation detecting probe ratios comparing the baboon polyclonal antisera and the goat polyclonal antisera were similar. Baboon CEA antisera ratios of 24, 48 and 72 hours were, respectively, 1.3, 1.4 and 1.6. Likewise, the goat polyclonal antibody localization ratios at 24, 48 and 72 hours were 1.2, 1.4 and 1.7, respectively. Gamma well tissue counts showed several levels of radioactivity comparing the baboon and goat polyclonal antibodies and showed similar distribution panels. This phase of the preliminary study demonstrated the ability for accurate tumor localization using either goat or baboon polyclonal antibody injected into the mouse model bearing a CEA-producing tumor.

In the initial investigation and studies which were carried out, Iodine 131 was used as the labelling isotope. The utilization of this isotope stemmed from its traditional use in conjunction with external imaging devices. The isotope has an 8.07 day half-life and 79% of it will exhibit photon energy levels of 365 kev, 6.7% of the isotope exhibits a 637 kev energy level; 5.9% of the isotope exhibits a 284 kev energy level; 2.6% of the isotope exhibits an 80 kev energy level and 1.8% thereof exhibits a 723 kev level. As is apparent, this is a relatively highly energetic isotope and its earlier election stems from the prior energy requirements of the external scanning devices.

Because of the immediate adjacency between the collimator of the probe of the instant invention with the organ being examined, it was determined that a lower level energy isotope should be investigated. In particular, Iodine 125 which has a lower energy of emission (35.5 kev) and an advantageously longer half-life (60 days) should be investigated. Accordingly, the capabilities of $I^{125}$-labelled CEA antibodies and $I^{131}$-labelled CEA antibodies to localized CEA producing colon cancer were compared in female Swiss nude mice bearing CX-1 human tumors implanted in one thigh. Emissions from two polyclonal antibodies (goat/baboon), one non-specific antibody (baboon), and one monoclonal antibody (mouse), all radiolabelled with $I^{125}$ or $I^{131}$ were recorded by the small probe of the invention and validated by a gamma well counter.

As a prelude to considering the results of this investigation, it should be observed that earlier models of the miniature probe were utilized in conjunction with human patients as is summarized hereinafter. $I^{131}$ radiolabels were used for these early operations. To detect neoplasm, an adequate ratio of the count values within a predetermined interval of time to background radiation was required. It was found that, using the above-described 20 second counting interval, ratios of about 1.8:1 were typically encountered and these ratios were sufficient for differentiating and localizing tumor. The use of the $I^{131}$ radiolabel also required that the operation take place at about 72 hours from the injection thereof into the patient. The waiting period permits the excretory system of the patient to remove as much background radiation as possible. However, the shorter, eight day half-life of the isotope did limit the time frame in which operations and preliminary investigations could be carried out.

The surgical procedure developed in utilizing the hand manipular probe of the invention involves a protocol commencing with the step of skin testing the patient with unlabelled anti-CEA antibody for allergic reactions. If the result of this test is negative, the patient is injected with the isotope labelled anti-CEA antibody.

Where combinations of higher energy isotope, i.e. $I^{131}$ labelled anti-CEA antibody also are injected, the patient is externally counted with the miniature probe as well as with an external scanner such as a gamma camera at given hourly periods following injection and the results are recorded. However, where the noted $I^{125}$ is utilized as the isotope label, then a delay is commenced to permit the clearing of background radiation which generally occurs through the reticuloendothelial system. Where the body cavity is opened, the surgeon inspects the abdomen visually and palpitates the organs thereof with the hands. The hand manipular probe then is utilized to determine background and to find and differentiate tumor by holding the collimator of the probe adjacent the surface of a selected organ and commencing a predetermined interval count. Following the count interval, the count level is recorded and the probe is moved to another position. The ratios as above discussed are noted to differentiate the boundary of the tumor and the tumor is resected. Following resection of the tumor, the hand manipular probe again is utilized to survey the operative region in order to determine whether or not the completed resection was fully effective. Where the ratios remain high, additional exploration and material removal is carried out. Because different organs of the body take up the anti-CEA antibody in different amounts, the background determinations are made for each organ of the body. In effect, like tissue is compared with like tissue in performing surgery with the miniature probe.

In the course of the operation, the surgical protocol also looks to the recordation of the counts determined during the probe counting intervals for pre-excision and post-excision of tumor. Each of the following organs are examined in a given colonic surgical procedure: thyroid, liver (left side and right side), stomach, spleen, right colon, transverse colon, left colon, rectum, pelvic floor (right side and left side), aorta (high, mid and low), vena cava, bladder, pancreas, flanks (right side and left side). Additionally, for colonic surgery, the location of count value may be recorded on a schematic diagram of the liver-colon region.

Looking to Table A, the results of surgical procedures upon human patients are provided in abbreviated form. The individual surgical activities are identified by patient name, hospital number, present status as of Sept. 1, 1986, and disease category. Additionally, the clinical data report summarizes the patient's surgical history as well as diagnostic imaging procedures routinely conducted on patients. The antibody information may be incomplete for some patients but generally provides the type of antibody, isotope label utilized, labelling protocol, and injection details. Thereafter, the surgical findings are summarized along with the details of the probe and protocol employed for the particular patient. Detailed probe counts for various organs also are detailed in the clinical data report. The particular probe utilized during the surgical procedure is identified by model number and the clinical data is identified by the sponsor and assignee of this application.

The clinical data in Table A commences with the first patient subjected to the surgical methodology disclosed herein and continues with a total of about 28 surgeries out of over 160 surgeries which have been conducted in accordance with the novel procedure of the present invention. It is believed that the patients selected in Table A are quite representative of the entire human study project. Also, it should be understood that early surgeries reported in Table A were conducted when the surgical methodology still was being evolved. Necessarily, then, the use of the probe and the methodology was experimental and an adjunct to conventional surgical protocols which determined the surgery. Later, after the procedure had been fully validated by the human studies, the surgical protocol of the present invention became part of the accepted protocol for the surgical procedures. Thus, the later data will be more representative of the surgical methodology as disclosed and claimed in this application.

The following abbreviations are used in Table A:
P/N is Positive or Negative
BX is Biopsy
AP is Anterior to Posterior
PA is Posterior to Anterior
C—C is Axis to Axis Patient JN was a 58 year old male who previously had a colon tumor removed. As the diagnosis information indicates, he had a mass on the neck near the thyroid cartilage. This mass was palpable and thought to be recurrent colon cancer even though in an unusual location. A bone scan (identified "BONE-SCAN") suggested that presence of tumor. The patient was injected with a polyclonal antibody (Haagensen). It will be seen that the first 30 patients were injected with this particular antibody. The tumor to background ratio (1) shows very close to a 1:1 relationship. In utilizing the hand manipular probe, the collimator tip thereof was held to the mass at the neck, ie. it was used externally. The unitary ratio indicates that the mass was not malignant. As shown at "SURG TYPE", the biopsy (Bx) of the mass showed no tumor to be present and the results verified the earlier indications of the hand manipular probe. Note that the preoperation tests included the above-noted bone scan as weel as a CAT-SCAN showing a positive mass in the neck and liver spleen (LS) scan which was negative. A CEA scan was negative after 24 and 96 hours. The post-operative CEA level of this patient was 2.3 The noted bone scan is a conventional variety utilizing technetium as the isotope. It is utilized mostly for detection of metastatic tumor. The CAT-SCAN designation is a conventional computer axial tomography scan looking to differing densities of tissue. Where the densities of a given organ and any tumor therewithin are substantially close in value, the CAT-scan information is of negligible value. The device has been found to be poor in tumor prediction. Under the term "OTHER" a needle or aspiration biopsy showed a negative result. "Lugols" is an iodine solution which blocks the thyroid in a manner protecting it from the $I^{131}$ label.

Patient IC was a 76 year old female who had a sigmoid tumor removed in 1982. She was evaluated inasmuch as the tumor marker CEA was suddenly increasing. All of the time honored scans as outlined above showed a negative result. The CEA baseline following surgical removal for the patient was about 2 as opposed to the pre-operation 19.3 value. Exploratory surgery revealed a tumor background ratio of 1:6:1 which, for the $I^{131}$ isotope, indicates the presence of tumor and the exploration resulted in the resection of a large tumor in the liver. Following removal of the tumor, the probe again was used and no counts exceeded 100 (background).

Patient CW was a 76 year old male who had a colon cancer removed in 1982 and at the time of this procedure showed an elevated CEA. Note that all of the conventional external scanning techniques showed negative results. The surgical re-exploration showed tumor recurrence in the liver and the small bowel. These tumors were of considerable size, much larger than 2 cm. The tumor/background ratio at the liver was 1.9:1, however the ratio in one of the small bowel tumors was 3:1. The ratio in the other small bowel tumor was 1.5:1. This may provide an indication of the heterogeneity of tumors and an indication as to why external scanners pick up some tumors but not others, notwithstanding the size of such tumors. It further might be noted that the size of the tumor in the liver was about that of a grapefruit and yet the external scanning devices did not detect it. The liver tumor was not removed in this 76 year old man.

Patient JS was a 59 year old male who had a primary tumor. External scanning showed only that there may have been a tumor involving the posterial wall of the bladder. Indeed, tumor was found to be at that location. This was a metastatic nodule and it is of interest that the external scanning did not detect the primary tumor which had a mass of about four times that of the metastatic tumor. Note that the tumor/background ratio was 2.1:1 which was found to be acceptable for $I^{131}$ labelling. Post resection scanning with the hand manipular probe showed essentially a unitary ratio. The post-operational CEA returned to a lower normal baseline value.

Patient RS was a 42 year old male who exhibited a pre-op CEA of 76.6. All external scans and other tests were negative. The patient had had a primary resection of colon cancer in 1979. At exploration, the tumor found was in the liver and was determined to be so large as to preclude resection. The hepatic artery was ligated and a portal vein catheter was placed. The post-operative CEA dropped to a low level of about 20. This same patient was re-admitted to the hospital and another procedure was carried out. Looking to that second procedure, large additional tumor in the liver were resected. During this surgery, the hand manipular probe indicated a higher tumor/background ratio in the adjacent diaphragm in the vicinity of the liver but not elsewhere. For that reason, a segment of the diaphragm itself was resected. This suspect area of the diaphragm evidenced no abnormality by palpation or vision, yet the probe and methodology located neoplastic tissue as confirmed by the histological report. In 1986, the patient still has a CEA level of 0.5 This is to be compared with a CEA level that went as high as 180 during procedure 9.1. All post resection counts using the probe showed a 1:1 ratio.

Patient JB was a 43 year old woman who had previously had two primary tumors, one a primary breast tumor which was removed by mastectomy and a primary tumor on the colon which was resected. As the pre-op results indicate, the bone scan was considered to respond to a stable metastatic tumor. However, the CEA scan did show a mass in the right chest area, a positive indication of tumor. The CAT-SCAN and liver speen scans were negative. The probe confirmed the presence of a tumor at the chest wall which was resected. Following the initial resection of this tumor, the probe indicated additional tumor and the tissue differentiated by the probe was removed. Following this removal, the tumor/background ratio returned to unity. The margin of the tumor, thus, was determined by the novel surgical methodology.

Patient VW was a 63 year old woman who had previously had an abdominal perineal resection. While her CEA had a value of 2.5, she had become symptomatic. A tumor could be observed within the posterial wall of the vagina. An intravaginal use of the probe confirmed the presence of this tumor following the injection of a relatively higher dose of $I^{131}$ labelled polyclonal antibody. Careful blockage with Lougols was carried out. The tumor/background ratio during the surgical procedure as well as during exploration preoperatively was about 1.8:1. During this surgical procedure, the probe was utilized to determine how much tissue in the pelvis was to be resected. Removal of material continued until the ratio became unity. To achieve this ratio, material had to be removed from pelvic bone. This material would not have been detected by conventional palpation or vision. No recurrence was detected in this patient as of eight months following the surgery.

Patient RA was a 73 year old woman who presented a rising CEA having a pre-operative value of 30.4. Even though the CAT-SCAN showed her to be normal, the CEA-scan showed her to be normal and the bone scan showed here to be normal, but the liver spleen scan suggested tumor. Exploratory surgery utilizing the probe for detection resulted in the removal of a tumor about the size of an orange from the liver. The tumor background ratio was 2:1 and the probe was utilized after the resection and indicated unity ratio. It may be observed that the earlier-discussed model 4 of the probe as described above commenced to be used at this point in time. Because of the angled shape of the collimator, background radiation was not encountered as the probe was manipulated beneath organs.

Patient MM was a 60 year old woman who had a primary colon tumor and also one in the liver. Note the lower levels of CEA. The large tumor/background ratio was observed in the hepatic lesion. Following the excising of the tumor from the liver, the count ratio thereat became unity.

Patient WE was a 50 year old male who presented a very aggressive signet cell tumor. A CEA external scan showed no tumor in the rectal mass but did show tumor along the aorta. The signet tumor was removed and the probe identified tumorous nodes along the aorta. His post-operative CEA was in the 1.2 to 1.8 range in January of 1984 but since that time has risen significantly. It is opinioned by the surgeon that the use of the later discussed $I^{125}$ labelling would have improved resection procedures in this case. Re-exploration at a later time revealed carcinomatosis.

Patient RP demonstrates the use of two radiolabels in conjunction with polyclonal antibody. Note that the isotopes $I^{131}$ as well as $I^{125}$ were used, the former being intended for external scanning and the latter for probe utilization. The latter utilization provided a tumor/background ratio of 6:1. All external scans in this case were negative. A right colon tumor was removed from this patient. Following resection of this tumor, the ratio became unity.

Patient KP was a 72 year old man who was administered polyclonal antibodies with dual isotopes (not shown). A rectal cancer was removed and a probe tumor/background ratio of 10:1 was developed. Post-resection showed a unity ratio. Such rectal tumors are known not to be particularly effective producers of CEA.

Patient JP was a 72 year old man who was operated upon for a liver tumor. This tumor had become almost necrotic and the in vivo tumor/background ratio identifying it with the probe was 3.5:1. However, when the tumor was removed and placed upon a table for ex vivo examination, the noted 10:1 ratio was derived. Note additionally that only $I^{125}$ labelled antibody was administered and that the dosage was relatively higher at 3.0 mCi. A monoclonal antibody was utilized with this isotope. Improved differentiation was realized with the monoclonal antibody.

Patient CM was a 71 year old male who was studied for a mass in his rectum. He was administered whole membrane antibody labelled both $I^{131}$ and $I^{125}$ (2.8/3.0 ratio, respectively). A five-day interval between injection and surgery ensued. The model 7 probe was utilized for the procedure.

Patient TB was a male who was being subjected to second look rectal surgery due to his evidencing a rising CEA value. Whole membrane antibody labelled both with $I^{131}$ and $I^{125}$ (1.91/2.41 ratio, respectively) was utilized three days prior to surgery. Again, the model 7 probe was utilized during surgery.

Patient MP was a female who previously had had primary and second look surgery performed. She was studied again to her evidencing a rising CEA value. Whole antibody labelled both with $I^{131}$ and $I^{125}$ (3.3/2.3 ratio, respectively) was utilized 11 days prior to surgery. When both isotopes were counted in the liver, values of about 22–30 were experienced. When the $I^{131}$ kev values were windowed out by the model 7 probe, the background liver tissue counts dropped to about 7, thus making a much improved tumor/background ratio possible.

Patient VK was a male who was studied due to a mass in the colon. The whole membrane antibody 17-1A was labelled with both $I^{131}$ and $I^{125}$ (3.3/2.34 ratio, respectively) and administered three days prior to surgery. After the primary colon and the tumor was removed, adjacent nodes were visualized and palpated by the surgeon. By such conventional protocol, the surgeon believed that these nodes were suspicious and may be diseased. The model 7 probe, however, evidenced no higher counts for the nodes. Samples of the nodes were removed and sent to pathology for histological evaluation. The frozen sections confirmed the protocol and probe determination that the suspicious nodes were not cancerous. Thus, the methodology of the present invention in this patient permitted healthy tissue, i.e. nodes, not to be surgically removed and such determination was not conclusive by a conventional surgical protocol.

Patient JR was a male who was studied due to a mass in the colon. Whole polyclonal baboon antibody was labelled with $I^{125}$ and administered four days prior to surgery. The methodology of the present invention confirmed the margins around the tumor for the surgeon.

Patient OH was a female who was studied for primary colon cancer. A fragment antibody was labelled with $I^{125}$ and presented to the patient two days prior to surgery. A left colectomy was performed during the surgery. Importantly, the surgical approach was drastically altered by the surgical methodology of the present invention. The surgeon found skip lesions (lymph nodes) adjacent to the suture line which tissue later was confirmed by frozen section to be cancerous. Such lesions, not adjacent to the primary tumor, were not suspicious by vision and palpation to the surgeon. It is to be noted that upon in vivo determination of these skip lesions by the model 7 probe, sample tissue was subjected to ex vivo analysis which again confirmed the precise location of the cancerous tissue within the sample removed. Based upon such ex vivo determination of the tissue, the probe-determined sites were subjected to histological analysis and the frozen sections confirmed the presence of neoplastic tissue. Thus, an additional invaluable tool was provided to the pathologist for more reliably determining the location whereat histological analysis during surgery would be performed. Such improved ex vivo procedure permits the course of surgery to be altered by the unique cooperative effort introduced between the pathologist and the surgeon in accordance with the methodology of the present invention. A final point is that fragment antibodies tend to have very short useful lifespans within the body so that surgery cannot be delayed too long following administration of the antibody to the patient.

Patient AW was a female who was studied for second look surgery due to evidencing a rising CEA value. A fragment antibody labelled with $I^{125}$ was administered four days prior to surgery. The model 9 probe containing the larger crystal was utilized for this surgery. Counts were taken for a five second interval. Examination of the abdomen revealed that the kidney evidenced much higher counts than other organs located within the abdomen. It is theorized that the body metabolizes fragment antibodies via renal functions within the kidney. Again, a mesenteric node was excised solely due to the surgical methodology employed utilizing the miniature probe during this surgery. Additionally, ex vivo counts of sample tissue was utilized for improving the ratio of neoplastic tissue to background and such ex vivo determination was quite helpful to the surgeon.

Patient KG was a 27 year old female who was subjected to second look surgery due to her evidencing a rising CEA value. $I^{125}$ labelled whole antibody was administered five days prior to surgery. Upon removal of the metastatic colon mass during surgery, replacement of the probe adjacent the tumro bed indicated that neoplastic tissue still was present. The tumor bed did not appear suspicious by vision and palpation to the surgeons. Additional tissue removed from the tumor bed was confirmed by pathology to be neoplastic. After the tumor bed was determined to be free of tissue by the utilization of the miniature probe, surgery was determined to be complete. The subclinical tissue removed during this procedure would not have been removed but for the surgical methodology of the present invention.

Patient LB was a 48 year old male who was studied for second look surgery due to his evidencing a rising CEA value. $I^{125}$ labelled whole antibody was administered four days prior to surgery. Upon accessing the surgical field, the surgeons determined that the second look surgery was negative, i.e. that no neoplastic tissue was present within the patient. The inventive surgical methodology of the present invention, however, found thickened mesentery tissue in the small bowel which evidenced counts consistent with the presence of neoplastic tissue. Samples were removed from the small bowel and sent to pathology for confirmation of neoplastic tissue. The initial histological report based upon frozen sections stated that no neoplastic tissue was present in the sample. Thereafter, the surgeon carried the probe to the pathology department and conducted ex vivo examination of the tissue. Such ex vivo examination determined a situs whereat neoplastic tissue was present in accordance with the methodology. Histological analysis of this situs confirmed the presence of diseased tissue. Thus, the surgical approach for this patient was radically altered in accordance with the methodology of the present invention and this patient owes the removal of cancer solely due to such novel surgical methodology.

Patient CR was a 59 year old male who was studied for second look surgery due to his evidencing a rising CEA value. $I^{125}$ labelled whole antibody was administered six days prior to surgery. This patient's primary surgery was an abdomenal peroneal resection following which chemotherapy on the patient was conducted. Upon accessing the surgical field, the surgeon's examination was inconclusive as to whether additional tumor was present. The surgical methodology was utilized in order to select samples which the probe determined were cancerous. Tissue was biopsied and submitted to pathology for histological analysis. Even though the initial pathology report was negative, the surgeons performed a resection based upon the probe and surgical methodology of the present invention. Permanent frozen section analysis two days later reported that the samples were positive, i.e. cancer was confirmed. Thus, it will be appreciated that the surgical methodology of the present invention again was responsible for altering the surgical approach initially planned for this patient. Also, the importance of utilizing the surgical methodology in ex vivo examination of tissue samples is demonstrated.

Patient MS was a male who was studied for recurrent tumor in the pelvis. A different whole antibody was labelled with $I^{125}$ and administered to the patient 11 days prior to surgery. This patient already had had an abdomenal peroneal resection. Samples taken during this exploratory surgery were subjected to histological analysis. The biopsies determined that the tissue was negative. Colon tissue still was removed based upon the new model 9 probe. A second surgery was performed in te peroneal area and probe-directed samples submitted to pathology which confirmed the presence of adenocarcinoma. Thereafter, rods were placed in the patient for radiotherapy. The progress of the shrinkage of the tumor then was followed by utilizing the probe in the peroneal area of the patient. Even after one month post-injection of the labelled antibody, the probe still could determine the presence of neoplastic tissue and, thus, the need for continued radiotherapy. 35 days after injection, the probe and methodology determined that no further neoplastic tissue was present and that the radiotherapy had been successful. As of the date of the clinical data report in Table A, the patient still is asymptomatic.

Patient RM was a female who had had a previous lower anterior resection, but was studied for second look surgery due to her evidencing a rising CEA value. Whole monoclonal antibody labelled with $I^{125}$ was administered to this patient 21 days prior to surgery. External peroneal counts were consistent with the presence of neoplastic tissue. Based upon this determination, trassacral surgery was determined to be the appropriate surgical approach rather than accessing the tissue through the abdomen. Biopsy samples determined by the probe and methodology were confirmed to be neoplastic by histological analysis. Radiation therapy, then, was determined to be the appropriate treatment for this patient. It is important to not that this patient required only one day of hospitalization because the methodology of the present invention permitted a much less extensive peroneal surgery to be performed, rather than the traditional abdomen surgery which would have required the patient to be hospitalized for an extended period of time.

Patient JN is a female who was studied for a presacral mass and her evidencing a rising CEA value. Whole monoclonal antibody labelled with $I^{125}$ was administered 13 days prior to an exploratory laporotemy. The surgeon could find no pelvic tumor, yet the probe determined that the left pelvic wall contained tumor whereas the right pelvic wall did not. Upon disection of the left pelvic wall, the revealed tissue evidenced extremely high counts. The cancerous retroiliac node was removed by surgeons.

One month later, this same patient was subjected to a right upper lobecetomy and a nodule on her lung located. After resection, the tumor bed again was examined with the model 9 probe and a subclinical lymph node determined to be cancerous. This finding was confirmed by the biopsy. The area of the resection, i.e. tumor margin, was precisely determined by the probe and surgical methodology of the present invention. Upon this second surgery, the patient again evidenced a normal CEA value.

Patient HK was studied for a primary breast mass. She was administered $I^{125}$ labelled whole monoclonal antibody 12 days prior to surgery. Externally, the surgeon could not locate the mass, though a positive mammogram was determined by diagnostic imaging. A left mastectomy and auxiliiary disection was performed on this patient. Probe-directed tissue determined to be cancerous in vivo was subjected to ex vivo analysis which clearly confirmed the presence of neoplastic tissue. These biopsied samples were subjected to frozen section to confirm the presence of intraductal breast cancer with no invasion. Additional subclinical deposits, lymph nodes, were determined by the probe to be neoplastic and were removed until the probe determined that no further neoplastic tissue was present. The final pathological report confirmed that all of the neoplastic tissue had been excised by the surgeon.

Patient EW was a male whos was studied for the presence of a liver tumor. Whole monoclonal antibody was administered 14 days prior to surgery and the model 9 probe was utilized. Due to the delay in surgery for 14 days, the liver had been virtually cleared of all unbound labelled antibody so that the surgeon could easily differentiate the multiple metastatic liver tumors present in this patient. In prior surgeries wherein surgery was delayed for only about 2–4 days following administration of the labelled antibody, the liver had not been fully cleared of unlabelled antibody so that differentiation of diseased tissue was more of a challenge for the surgeon. This procedure demonstrates the unexpected yet efficacious results which are realized when surgery is delayed for time periods much greater than those taught in the nuclear medicine art. Surgical determination of neoplastic tissue is much improved by utilizing the surgical delay time interval as part of the surgical methodology.

TABLE A

NEOPROBE HUMAN STUDIES - CLINICAL DATA REPORT
09/05/86
PATIENT NAME: J N          HOSPITAL NUMBER: 900-88-3615
PRESENT STATUS AS OF 09/01/86: ALIVE WITHOUT CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 07/08/83 | CHEST X-RAY | N | | |
| 07/13/85 | BONE SCAN | P | MASS ON MANUBRIUM | FP |
| 07/15/83 | ANTIBODY | N | NO INCREASED ACTIVITY | TN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 01/11/77 | L COLON RESECTION | N |
| 07/15/83 | BX OF MASS ON MANUBRIUM | Y |

PATIENT NAME: J N
DETAILED INFORMATION FOR SURGERY DATE: 07/15/83
RESAON FOR STUDY: MASS ON MANUBRIUM
ANTIBODY INFORMATION
ANTIBODY: Anti-CEA Whole IgG from DR. HAAG
BEFORE LABELING
Protein:   0.0 mg/ml   Method:
LABELING
Date: 07/12/83   Time:   Isotope: I-131
Activity added:   0.00 mCi
Concentration:
AFTER LABELING
% BOUND: 0.0%
Isotope Removal Method:
Protein:   0.0 mg/ml   Method:
Affinity:                   Method:
INJECTION
Date: 07/12/83   Time: 15:00
Activity:   1.75 mCi   VOLUME: 0.0 mls SURGERY
Date: 07/15/83   Time: 14:45

TABLE A-continued

Operation: BX OF MASS ON MANUBRIUM
Findings: NO TUMOR
Histological Report:MANUBRIUM MASS-FIBROSIS TISSUE
PROBE
Model: MODEL 2
Counting Duration: 20 sec    Collimation:
Surgical approach was not altered by probe use.
Comments: COUNTS OF MASS WERE SIMILAR TO NORMAL TISSUE

PATIENT NAME: J N
PROBE COUNTS

| TISSUE | AP/PA/C—C | INVIVO/INVITRO | MEAN COUNT |
|---|---|---|---|
| ROOM BACKGROUND | | | 0.00 |
| THYROID | AP | OUT | 57.00 |
| MANUBRIUM MASS-T1 | AP | OUT | 75.00 |
| STERNUM-B1 | AP | OUT | 76.67 |
| XYPHOID | AP | OUT | 94.00 |
| LIVER | AP | OUT | 98.50 |
| ABDOMEN | AP | OUT | 71.33 |

Tumor/Background Ratio:
1 - 0.98

NEOPROBE HUMAN STUDIES - CLINICAL DATA REPORT
09/05/86
PATIENT NAME: I C            HOSPITAL NUMBER: 900-19-1017
PRESENT STATUS AS OF 09/01/86: EXPIRED
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 07/14/83 | BONE SCAN | N | | |
| 07/14/83 | BARIUM ENEMA | N | | TN |
| 07/18/83 | CAT - ABDOMINAL | N | NO METASTATIC DISEASE | FN |
| 07/18/83 | ANTIBODY | N | NO TUMOR IMAGED | FN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 01/01/82 | L COLON RESECTION | N |
| 01/11/81 | SIGMOID RESECTION | N |
| 07/18/83 | R WEDGE RESECTION & L LATERAL SEGMENTECTOMY | Y |

PATIENT NAME: I C
DETAILED INFORMATION FOR SURGERY DATE: 07/18/83
REASON FOR STUDY: RISING CEA
ANTIBODY INFORMATION
ANTIBODY: Anti-CEA Whole IgG from DR. HAAG
BEFORE LABELING
Protein:   0.0 mg/ml   Method:
LABELING
Date: 07/14/83         Time:        Isotope: I-131
Activity added:         0.00 mCi
Concentration:
AFTER LABELING
% BOUND: 0.0%
Isotope Removal Method:
Protein:   0.0 mg/ml   Method:
Affinity:                          Method:
INJECTION
Date: 07/14/85         Time: 12:00
Activity:    2.34 mCi      VOLUME: 0.0 mls SURGERY
Date: 07/18/83         Time: 07:30
Operation: R WEDGE RESECTION & L LATERAL SEGMENTECTOMY
Findings: TUMOR CONFINED TO LIVER
Histological Report: LIVER-ADENOCARCINOMA
PROBE
Model: MODEL 1, NICKEL PROBE
Counting Duration: 20 sec    Collimation: 0
Surgical approach was not altered by probe use.
Comments: TUMOR COUNTS WERE HIGHER THAN NORMAL TISSUE

PATIENT NAME: I C
PROBE COUNTS

| TISSUE | AP/PA/C—C | INVIVO/INVITRO | MEAN COUNT |
|---|---|---|---|
| SPLEEN | AP | IN | 82.00 |
| LIVER-(B2) | AP | IN | 82.00 |
| R LIVER TUMOR-(T2) | AP | IN | 131.00 |
| L LIVER TUMOR-T1 | AP | IN | 167.00 |

TABLE A-continued

| | | | |
|---|---|---|---|
| LIVER-B1 | AP | IN | 82.00 |
| COLON | AP | IN | 58.00 |
| L LIVER TUMOR BED | AP | IN | 98.00 |
| R LIVER TUMOR BED | AP | IN | 90.00 |

Tumor/Background Ratio:
1 - 2.04
(2) - 1.60

NEOPROBE HUMAN STUDIES - CLINICAL DATA REPORT
09/05/86
PATIENT NAME: C W    HOSPITAL NUMBER: 900-22-2207
PRESENT STATUS AS OF 09/01/86: EXPIRED
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 07/05/83 | CHEST X-RAY | N | | |
| 07/05/83 | ANTIBODY | N | NO TUMOR IMAGED | FN |
| 07/14/83 | BONE SCAN | N | | |

Index damaged. REINDEX should be done before using data.
LAB TESTS
DATE   TEST                                    RESULTS

SURGICAL HISTORY

| DATE | PROCEDURE | PROBE USED |
|---|---|---|
| 07/08/83 | EXP LAP, EXCISION OF MESENTERIC MASS | Y |
| 12/27/82 | COLON RESECTION | N |

PATIENT NAME: C W
DETAILED INFORMATION FOR SURGERY DATE: 07/08/83
REASON FOR STUDY: RISING CEA
ANTIBODY INFORMATION
ANTIBODY: Anti-CEA Whole IgG from DR. HAAG
BEFORE LABELING
Protein:   0.0 mg/ml    Method:
LABELING
Date: 07/05/83    Time:    Isotope I-131
Activity added:      0.00 mCi
Concentration:
AFTER LABELING
% BOUND: 0.0%
Isotope Removal Method:
Protein:   0.0 mg/ml    Method:
Affinity:                        Method:
INJECTION
Date: 07/05/83    Time: 13:00
Activity:   1.60 mCi    VOLUME: 3.4 mls SURGERY
Date: 07/08/83    Time: 11:45
Operation: EXP LAP, EXCISION OF MESENTERIC MASS
Findings: DIFFUSE METASTASIS THROUGHOUT LIVER & MESENTERY
Histological Report: MESENTERIC BIOPSY-METASTATIC CARCINOID TUMOR
PROBE
Model: MEDOL 1, NICKEL PROBE
Counting Duration:       20 sec   Collimation:
Surgical approach was not altered by probe use.
Comments: TUMOR COUNTS HIGHER THAN NORMAL TISSUE

PATIENT NAME: C W
PROBE COUNTS

| TISSUE | AP/PA/C—C | INVIVO/INVITRO | MEAN COUNT |
|---|---|---|---|
| ROOM BACKGROUND | | | 2.00 |
| LIVER-B1 | AP | IN | 148.00 |
| LIVER TUMOR-T1 | AP | IN | 308.00 |
| MESENTERY-(B2) | AP | IN | 88.00 |
| MESENTERIC TUMOR-(T2) | AP | IN | 259.50 |
| STOMACH | AP | IN | 249.00 |
| SPLEEN | AP | IN | 119.00 |
| R GUTTER | AP | IN | 120.00 |
| L GUTTER | AP | IN | 79.00 |
| COLON | AP | IN | 174.00 |
| AORTA | AP | IN | 247.00 |

Tumor/Background Ratio:
1 - 2.08
2 - 2.95

NEOPROBE HUMAN STUDIES - CLINICAL DATA REPORT
09/05/86
PATIENT NAME: J S    HOSPITAL NUMBER: 900-73-9307
PRESENT STATUS AS OF 09/01/86: EXPIRED
DISEASE CATEGORY: Rectal CA TABLE A-continued DIAGNOSTIC IMAGING
| DATE | SCAN | P/N | INTERPRETATION OF SCAN | CORRELATION |
|---|---|---|---|---|
| 05/04/83 | BARIUM ENEMA | P | MASS IN RECTUM | TP |
| 05/10/83 | COLONOSCOPY | P | MASS IN RECTUM | TP |
| 05/11/83 | LIVER/SPLEEN | N | | TN |
| 05/13/83 | BONE SCAN | P | | |
| 05/16/83 | ANTIBODY | P | MASS BEHIND BLADDER | TP |

Index damaged. REINDEX should be done before using data.
LAB TESTS
DATE    TEST                                                  RESULTS SURGICAL HISTORY
| DATE | PROCEDURE | PROBE USED |
|---|---|---|
| 05/16/83 | A-P RESECTION | Y |

PATIENT NAME: J S
DETAILED INFORMATION FOR SURGERY DATE: 05/16/83
REASON FOR STUDY: MASS IN RECTUM
ANTIBODY INFORMATION
ANTIBODY: Anti-CEA Whole IgG from DR. HAAG
BEFORE LABELING
Protein:   0.0 mg/ml    Method:
LABELING
Date: 05/13/83         Time:         Isotope: I-131
Activity added:        0.00 mCi
Concentration:
AFTER LABELING
% BOUND: 0.0%
Isotope Removal Method:
Protein:   0.0 mg/ml    Mehtod:
Affinity:                           Method:
INJECTION
Date: 05/13/83         Time: 13:20
Activity:   1.20 mCi    VOLUME: 0.0 mls SURGERY
Date: 05/16/83         Time: 11:00
Operation: A-P RESECTION
Findings: LARGE RECTAL MASS
Histological Report:ANUS-SQUAMOUS CELL CANCER
PROBE
Model: MODEL 1, NICKEL PROBE
Counting Duration:        20 sec    Collimation:    0
Surgical approach was not altered by probe use.
Comments: DETERMINED AREAS OF RESECTION PATIENT NAME: J S
PROBE COUNTS
| TISSUE | AP/PA/C—C | INVIVO/INVITRO | MEAN COUNT |
|---|---|---|---|
| RECTAL TUMOR-T1 | AP | IN | 45.00 |
| COLON-B1 | AP | IN | 22.00 |

Tumor/Background Ratio:
1 - 2.05

NEOPROBE HUMAN STUDIES - CLINICAL DATA REPORT
09/05/86
PATIENT NAME: R S          HOSPITAL NUMBER: 900-21-7931
PRESENT STATUS AS OF 09/01/86: ALIVE WITHOUT CA
DISEASE CATEGORY: L Colon/Sigmoid CA DIAGNOSTIC IMAGING
| DATE | SCAN | P/N | INTERPRETATION OF SCAN | CORRELATION |
|---|---|---|---|---|
| 06/17/83 | ANTIBODY | N | NO TUMOR IMAGED | FN |

Index damaged. REINDEX should be done before using data.
LAB TESTS
DATE    TEST                                                  RESULTS SURGICAL HISTORY
| DATE | PROCEDURE | PROBE USED |
|---|---|---|
| 01/01/78 | SIGMOID RESECTION | N |
| 06/17/83 | EXP LAP, HAL & PVC | Y |
| 09/12/83 | R LIVER RESECTION & EXCISION OF R DIAPHRAGM | Y |

PATIENT NAME: R S
DETAILED INFORMATION FOR SURGERY DATE: 06/17/83
REASON FOR STUDY: RISING CEA
ANTIBODY INFORMATION
ANTIBODY: Anti-CEA Whole IgG from DR. HAAG
BEFORE LABELING
Protein:   0.0 mg/ml    Method:

TABLE A-continued

LABELING
Date: 06/14/83       Time:       Isotope: I-131
Activity added:       0.00 mCi
Concentration:
AFTER LABELING
% BOUND: 0.0%
Isotope Removal Method:
Protein:   0.0 mg/ml   Method:
Affinity:                          Method:
INJECTION
Date: 06/14/83      Time: 12:00
Activity:    2.06 mCi    VOLUME: 0.0 mls SURGERY
Date: 06/17/83      Time: 12:23
Operation: EXP LAP, HAL & PVC
Findings: TUMOR IN R LOBE OF LIVER INVADING R DIAPHRAGM
Histological Report: LIVER-METASTATIC ADENOCARCINOMA
PROBE
Model: MODEL 2
Counting Duration:        20 sec   Collimation:    0
Surgical approach was not altered by probe use.
Comments: TUMOR COUNTS WERE HIGHER THAN NORMAL TISSUE

PATIENT NAME: R S
PROBE COUNTS

| TISSUE | AP/PA/C—C | INVIVO/INVITRO | MEAN COUNT |
|---|---|---|---|
| ROOM BACKGROUND | | | 2.00 |
| AORTA | AP | IN | 138.00 |
| LIVER TUMOR-T1 | AP | IN | 168.00 |
| LIVER-B1 | AP | IN | 124.00 |
| SM BOWEL | AP | IN | 36.00 |
| OMENTUM | AP | IN | 38.00 |
| SPLEEN | AP | IN | 92.00 |
| COLON | AP | IN | 52.00 |
| L GUTTER | AP | IN | 24.00 |
| R GUTTER | AP | IN | 60.00 |
| R ILIAC FOSSA | AP | IN | 37.00 |
| L ILIAC FOSA | AP | IN | 27.00 |
| PANCREAS | AP | IN | 78.00 |
| THYROID | AP | OUT | 82.00 |
| XYPHOID | AP | OUT | 51.00 |
| LIVER | AP | OUT | 54.00 |
| L CHEST WALL | AP | OUT | 38.00 |
| BLADDER | AP | OUT | 37.00 |
| ABDOMEN | AP | OUT | 20.00 |

Tumor/Background Ratio:
1 - 1.35

NEOPROBE HUMAN STUDIES - CLINICAL DATA REPORT
09/05/86
PATIENT NAME: J B          HOSPITAL NUMBER: 900-17-5898
PRESENT STATUS AS OF 09/01/86: EXPIRED
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 03/15/83 | LIVER/SPLEEN | N | | |
| 03/16/83 | CHEST X-RAY | P | METASTATSIS TO SPINE | |
| 03/16/83 | BONE SCAN | P | STABLE METASTATIC DISEASE | |
| 03/23/83 | ANTIBODY | P | R CHEST WALL TUMOR IMAGED | TP |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 03/23/83 | EXCISION OF R CHEST WALL MASS | Y |
| 05/11/82 | BILATERAL OOPHRECTOMY | N |
| 08/11/79 | R COLON RESECTION | N |
| 11/11/79 | L RADICAL MASTECTOMY | N |
| 12/11/82 | BILATERAL ADREALECTOMY | N |

PATIENT NAME: J B
DETAILED INFORMATION FOR SURGERY DATE: 03/23/83
REASON FOR STUDY:
ANTIBODY INFORMATION
ANTIBODY: Anti-CEA Whole IgG from DR. HAAG
BEFORE LABELING
Protein:   0.0 mg/ml   Method:
LABELING
Date: 03/21/83       Time:       Isotope: I-131

TABLE A-continued

Activity added: 0.00 mCi
Concentration:
AFTER LABELING
% BOUND: 0.0%
Isotope Removal Method:
Protein: 0.0 mg/ml    Mehtod:
Affinity:                              Method:
INJECTION
Date: 03/21/83    Time: 13:00
Activity:    2.28 mCi    VOLUME: 0.0 mls SURGERY
Date: 03/23/83    Time: 13:00
Operation: EXCISION OF R CHEST WALL MASS
Findings: MASS CONSISTENT WITH METASTATIC BREAST CANCER
Histological Report: SOFT TISSUE, CHEST WALL-METASTATIC ADENOCARCINOMA
PROBE
Model: MODEL 2
Counting Duration:    20 sec    Collimation:    0
Surgical approach was altered by probe use.
Comments: DETERMINED AREAS OF RESECTION

PATIENT NAME: J B
PROBE COUNTS

| TISSUE | AP/PA/C—C | INVIVO/INVITRO | MEAN COUNT |
|---|---|---|---|
| CHEST WALL TUMOR-T1 | AP | IN | 77.00 |
| CHEST WALL-B1 | AP | IN | 40.00 |

Tumor/Background Ratio:
1 - 1.93

NEOPROBE HUMAN STUDIES - CLINCIAL DATA REPORT
09/05/86
PATIENT NAME: V W          HOSPITAL NUMBER: 900-03-6836
PRESENT STATUS AS OF 09/01/86: EXPIRED
DISEASE CATEGORY: Rectal CA

DIAGNOSTIC IMAGING

| DATE | SCAN | P/N | INTERPRETATION OF SCAN | CORRELATION |
|---|---|---|---|---|
| 08/05/83 | LIVER/SPLEEN | N | | TN |
| 08/08/83 | BONE SCAN | N | | |
| 08/08/83 | BARIUM ENEMA | N | | TN |
| 08/08/83 | CAT - ABDOMINAL | N | TUMOR IN PELVIS | FN |
| 08/10/83 | ANTIBODY | N | NO TUMOR IMAGED | FN |

Index damaged. REINDEX should be done before using data.
LAB TESTS
DATE    TEST                                    RESULTS

SURGICAL HISTORY

| DATE | PROCEDURE | PROBE USED |
|---|---|---|
| 02/01/82 | A-P RESECTION | N |
| 08/12/83 | TOTAL CYSTECTOMY, PARTIAL VAGINECTOMY | Y |

PATIENT NAME: V W
DETAILED INFORMATION FOR SURGERY DATE: 08/12/83
REASON FOR STUDY: PELVIC MASS FOUND BY EXAM.
ANTIBODY INFORMATION
ANTIBODY: Anti-CEA Whole IgG from DR. HAAG
BEFORE LABELING
Protein: 0.0 mg/ml    Method:
LABELING
Date: 08/09/83    Time:    Isotope: I-131
Activity added:    0.00 mCi
Concentration:
AFTER LABELING
% BOUND: 0.0%
Isotope Removal Method:
Protein: 0.0 mg/ml    Method:
Affinity:                              Method:
INJECTION
Date: 08/09/83    Time: 13:30
Activity:    3.60 mCi    VOLUME: 0.0 mls SURGERY
Date: 08/12/83    Time: 12:20
Operation: TOTAL CYSTECTOMY, PARTIAL VAGINECTOMY
Findings: TUMOR IN PELVIS INVOLVING THE BLADDER
Histological Report: PELVIS-RECURRENT ADENOCARCINOMA
PROBE
Model: MODEL 3
Counting Duration:    20 sec    Collimation:
Surgical approach was not altered by probe use.
Comments: TUMOR COUNTS WERE HIGHER THAN NORMAL TISSUE

TABLE A-continued

PATIENT NAME: V W
PROBE COUNTS

| TISSUE | AP/PA/C—C | INVIVO/INVITRO | MEAN COUNT |
|---|---|---|---|
| AORTA | AP | IN | 71.00 |
| R OVARY | AP | IN | 34.00 |
| L OVARY | AP | IN | 45.00 |
| UTERUS | AP | IN | 61.00 |
| MESENTERY | AP | IN | 59.00 |
| LIVER | AP | IN | 99.00 |
| COLON | AP | IN | 62.00 |
| SMALL BOWEL | AP | IN | 62.00 |
| VENA CAVA | AP | IN | 74.00 |
| STOMACH | AP | IN | 79.00 |
| PELVIS-B1 | AP | IN | 40.00 |
| PELVIC TUMOR-T1 | AP | IN | 97.67 |
| KIDNEY | AP | IN | 55.00 |

Tumor/Background Ratio:
1 - 2.44

NEOPROBE HUMAN STUDIES - CLINICAL DATA REPORT
09/05/86
PATIENT NAME: R A          HOSPITAL NUMBER: 900-18-0042
PRESENT STATUS AS OF 09/01/86: EXPIRED
DISEASE CATEGORY: R Colon/Transverse CA

DIAGNOSTIC IMAGING

| DATE | SCAN | P/N | INTERPRETATION OF SCAN | CORRELATION |
|---|---|---|---|---|
| 08/29/83 | COLONOSCOPY | N | | TN |
| 08/29/83 | CHEST X-RAY | N | | |
| 08/29/83 | ANTIBODY | P | TUMOR IMAGED IN PELVIS | TP |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 01/01/83 | EXP LAP, MULTIPLE BIOPSIES | N |
| 01/10/78 | TRANSVERSE COLON RESECTION | N |
| 08/30/83 | EXP LAP, EXCISION OF PELVIC MASS, BX OF MESENTERY | Y |
| 10/01/81 | TOTAL ABDOMINAL HYSTERTECOMY | N |

PATIENT NAME: R A
DETAILED INFORMATION FOR SURGERY DATE: 08/30/83
REASON FOR STUDY: RISING CEA
ANTIBODY INFORMATION
ANTIBODY: Anti-CEA Whole IgG from DR. HAAG
BEFORE LABELING
Protein:   0.0 mg/ml   Method:
LABELING
Date: 08/26/83   Time:   Isotope: I-131
Activity added:   0.00 mCi
Concentration:
AFTER LABELING
% BOUND: 0.0%
Isotope Removal Method:
Protein:   0.0 mg/ml   Method:
Affinity                          Method:
INJECTION
Date: 08/26/83   Time: 13:40
Activity:   0.00 mCi   VOLUME: 0.0 mls SURGERY
Date: 08/30/83   Time: 08:00
Operation: EXP LAP, EXCISION OF PELVIC MASS, BX OF MESENTERY
Findings: 4 MASSES IN PELVIS
Histological Report:
PROBE
Model: MODEL 4
Counting Duration:        20 sec   Collimation:
Surgical approach was not altered by probe use.
Comments: TUMOR COUNTS HIGHER THAN NORMAL TISSUE

PATIENT NAME: R A
PROBE COUNTS

| TISSUE | AP/PA/C—C | INVIVO/INVITRO | MEAN COUNT |
|---|---|---|---|
| ROOM BACKGROUND | | | 0.00 |
| PELVIS TUMOR #1-T1 | AP | IN | 101.00 |
| PELVIS-B1 | AP | IN | 41.00 |
| PELVIC TUMOR #2-(T2) | AP | IN | 113.00 |
| PELVIS-(B2) | AP | IN | 43.00 |

Tumor/Background Ratio:

TABLE A-continued

1 - 2.46
(2) - 2.63

NEOPROBE HUMAN STUDIES - CLINICAL DATA REPORT
09/05/86
PATIENT NAME: M M            HOSPITAL NUMBER: 900-23-0166
PRESENT STATUS AS OF 09/01/86: ALIVE WITH CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 09/26/83 | COLONOSCOPY | P | L SIDED COLON MASS | TP |
| 09/26/83 | LIVER/SPLEEN | N | | TN |
| 09/27/83 | BONE SCAN | N | | |
| 09/28/83 | ANTIBODY | P | COLON TUMOR IMAGED | TP |

Index damaged. REINDEX should be done before using data.
LAB TESTS
DATE   TEST                                         RESULTS

SURGICAL HISTORY

| DATE | PROCEDURE | PROBE USED |
|---|---|---|
| 09/30/83 | L COLON RESECTION, BIOPSY OF LIVER & HAL | Y |

PATIENT NAME: M M
DETAILED INFORMATION FOR SURGERY DATE: 09/30/83
REASON FOR STUDY: MASS IN COLON
ANTIBODY INFORMATION
ANTIBODY: Anti-CEA Whole IgG from DR. HAAG
BEFORE LABELING
Protein:    0.0 mg/ml    Method:
LABELING
Date: 09/26/83       Time:        Isotope: I-131
Activity added:      0.00 mCi
Concentration:
AFTER LABELING
% BOUND: 0.0%
Isotope Removal Method:
Protein:    0.0 mg/ml    Method:
Affinity:                         Method:
INJECTION
Date: 09/26/83       Time: 15:00
Activity:      1.86 mCi VOLUME: 0.0 mls SURGERY
Date: 09/30/83      Time:
Operation: L COLON RESECTION, BIOPSY OF LIVER & HAL
Findings: COLON TUMOR AND METASTASIS TO LIVER
Histological Report: COLON & LIVER TUMORS & LYMPH NODES-ADENOCARCINOMA
PROBE
Model: MODEL 4
Counting Duration:       20 sec   Collimation:    0
Surgical approach was not altered by probe use.
Comments: HIGH BACKGROUND COUNTS, I.E., AORTA & LIVER

PATIENT NAME: M M
PROBE COUNTS

| TISSUE | AP/PA/C—C | INVIVO/INVITRO | MEAN COUNT |
|---|---|---|---|
| AORTA | AP | IN | 289.33 |
| COLON-B1 | AP | IN | 107.67 |
| COLON TUMOR-T1 | AP | IN | 204.00 |
| LIVER-(B2) | AP | IN | 450.00 |
| LIVER TUMOR-(T2) | AP | IN | 576.33 |
| PELVIS | AP | IN | 108.00 |
| SPLEEN | AP | IN | 349.00 |

Tumor/Background Ratio:
1 - 1.89
(2) - 1.28

NEOPROBE HUMAN STUDIES - CLINICAL DATA REPORT
09/05/86
PATIENT NAME: W E            HOSPITAL NUMBER: 900-12-6144
PRESENT STATUS AS OF 09/01/86: EXPIRED
DISEASE CATEGORY: Rectal CA

DIAGNOSTIC IMAGING

| DATE | SCAN | P/N | INTERPRETATION OF SCAN | CORRELATION |
|---|---|---|---|---|
| 10/24/83 | ANTIBODY | N | NO RECTAL TUMOR IMAGED | FN |

Index damaged. REINDEX should be done before using data.
LAB TESTS
DATE   TEST                                         RESULTS

SURGICAL HISTORY

TABLE A-continued

| DATE | PROCEDURE | PROBE USED |
|---|---|---|
| 01/09/84 | EXP LAP | N |
| 10/24/83 | A-P RESECTION | Y |

PATIENT NAME: W E
DETAILED INFORMATION FOR SURGERY DATE: 10/24/83
REASON FOR STUDY: MASS IN RECTUM
ANTIBODY INFORMATION
ANTIBODY: Anti-CEA Whole IgG from DR. HAAG
BEFORE LABELING
Protein: 0.0 mg/ml  Method:
LABELING
Date: 10/21/83  Time:  Isotope: I-131
Activity added:  0.00 mCi
Concentration:
AFTER LABELING
% BOUND: 0.0%
Isotope Removal Method:
Protein: 0.0 mg/ml  Method:
Affinity:  Method:
INJECTION
Date: 10/21/83  Time: 11:00
Activity: 1.00 mCi  VOLUME: 0.0 mls SURGERY
Date: 10/24/83  Time: 13:40
Operation: A-P RESECTION
Findings: METASTASIS TO LYMPH NODES & MESENTERY
Histological Report: COLON, LYMPH NODE & IMPLANTS - SIGNET CELL ADENCA.
PROBE
Model: MODEL 4
Counting Duration:  20 sec  Collimation:  0
Surgical approach was not altered by probe use.
Comments: TUMOR COUNTS WERE HIGHER THAN NORMAL TISSUE

PATIENT NAME: W E
PROBE COUNTS

| TISSUE | AP/PA/C—C | INVIVO/INVITRO | MEAN COUNT |
|---|---|---|---|
| COLON-B1 | AP | IN | 33.00 |
| COLON TUMOR-T1 | AP | IN | 59.00 |

Tumor/Background Ratio:
1 - 1.79

NEOPROBE HUMAN STUDIES - CLINICAL DATA REPORT
09/05/86
PATIENT NAME: R P  HOSPITAL NUMBER: 834-28-3400
PRESENT STATUS AS OF 09/01/86: ALIVE WITH CA
DISEASE CATEGORY: R Colon/Transverse CA

DIAGNOSTIC IMAGING

| DATE | SCAN | P/N | INTERPRETATION OF SCAN | CORRELATION |
|---|---|---|---|---|

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 11/18/83 | RIGHT COLON RESECTION | Y |

PATIENT NAME: R P
DETAILED INFORMATION FOR SURGERY DATE: 11/18/83
REASON FOR STUDY: MASS IN RIGHT COLON
ANTIBODY INFORMATION
ANTIBODY: Anti-CEA Whole IgA from DR. HAAG
BEFORE LABELING
Protien: 0.0 mg/ml  Method:
LABELING
Date: / /  Time:  Isotope: I-131
Activity added:  0.00 mCi
Concentration:
AFTER LABELING
% BOUND: 0.0%
Isotope Removal Method:
Protein: 0.0 mg/ml  Method:
Affinity:  Method:
INJECTION
Date: 11/15/83  Time:
Activity: 0.00 mCi  VOLUME: 0.0 mls SURGERY
Date: 11/18/83  Time: 08:00

TABLE A-continued

Operation: RIGHT COLON RESECTION
Findings: TUMOR CONFINED TO COLON
Histological Report:COLON MASS-ADENOCARCINOMA
PROBE
Model: MODEL 4
Counting Duration: 20 sec   Collimation:
Surgical approach was not altered by probe use.
Comments: TUMOR COUNTS HIGHER THAN NORMAL TISSUE

PATIENT NAME: R P
PROBE COUNTS

| TISSUE | AP/PA/C—C | INVIVO/INVITRO | MEAN COUNT |
|---|---|---|---|
| ROOM BACKGROUND | | | 0.00 |
| COLON TUMOR-T1 | AP | IN | 91.50 |
| COLON-B1 | AP | IN | 16.33 |
| LIVER | AP | IN | 75.50 |
| PANCREAS | AP | IN | 44.00 |

Tumor/Background Ratio:
1 - 5.60

NEOPROBE HUMAN STUDIES - CLINICAL DATA REPORT
09/05/86
PATIENT NAME: K P            HOSPITAL NUMBER: 275-03-6647
PRESENT STATUS AS OF 09/01/86: ALIVE WITHOUT CA
DISEASE CATEGORY: Rectal CA

DIAGNOSTIC IMAGING

| DATE | SCAN | P/N | INTERPRETATION OF SCAN | CORRELATION |
|---|---|---|---|---|
| 11/28/83 | BONE SCAN | N | | |
| 11/29/83 | COLONOSCOPY | P | MASS IN RECTUM | TP |
| 11/29/83 | LIVER/SPLEEN | N | | TN |
| 12/01/83 | CAT - ABDOMINAL | P | MASS IN SIGMOID COLON | TP |
| 12/02/83 | ANTIBODY | N | NO TUMOR IMAGED | FN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 12/05/83 | A-P RESECTION | Y |

PATIENT NAME: K P
DETAILED INFORMATION FOR SURGERY DATE: 12/05/83
REASON FOR STUDY: MASS IN RECTUM
ANTIBODY INFORMATION
ANTIBODY: Anti-CEA Whole IgG from DR. HAAG
BEFORE LABELING
Protein:   0.0 mg/ml   Method:
LABELING
Date: 11/28/83      Time:        Isotope: I-131
Activity added:    0.00 mCi
Concentration:
AFTER LABELING
% BOUND: 0.0%
Isotope Removal Method:
Protein:   0.0 mg/ml   Method:
Affinity:                        Method:
INJECTION
Date: 11/28/83     Time: 12:00
Activity:    1.10 mCi    VOLUME: 0.0 mls SURGERY
Date: 12/05/83     Time: 10:15
Operation: A-P RESECTION
Findings: TUMOR CONFINED TO COLON
Histological Report: COLON-ADENOCARCINOMA; LYMPH NODE-REACTIVE CHANGES
PROBE
Model: MODEL 4
Counting Duration: 20 sec   Collimation: 0
Surgical approach was not altered by probe use.
Comments: AREAS OF RESECTION COULD HAVE BEEN EASILY DEFINED

PATIENT NAME: K P
PROBE COUNTS

| TISSUE | AP/PA/C—C | INVIVO/INVITRO | MEAN COUNT |
|---|---|---|---|
| COLON TUMOR-T1 | AP | IN | 34.00 |
| COLON-B1 | AP | IN | 4.00 |
| LIVER | AP | IN | 24.00 |
| STOMACH | AP | IN | 8.00 |
| SPLEEN | AP | IN | 4.00 |

Tumor/Background Ratio:

TABLE A-continued

1 - 8.50

NEOPROBE HUMAN STUDIES - CLINICAL DATA REPORT
09/05/86
PATIENT NAME: J P          HOSPITAL NUMBER: 900-23-8805
PRESENT STATUS AS OF 09/01/86: EXPIRED
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 12/04/83 | ARTERIOGRAM | N | NO TUMOR BLUSH | FN |
| 12/07/83 | CHEST X-RAY | P | POSSIBLE LUNG METS | |
| 12/13/83 | CAT - CHEST | N | | |

Index damaged. REINDEX should be done before using data.

LAB TESTS

| DATE | TEST | UZ,30/36 RESULTS |
|---|---|---|

SURGICAL HISTORY

| DATE | PROCEDURE | PROBE USED |
|---|---|---|
| 01/11/79 | LEFT COLON RESECTION | N |
| 12/30/83 | LEFT LIVER RESECTION | Y |

PATIENT NAME: J P
DETAILED INFORMATION FOR SURGERY DATE: 12/30/83
REASON FOR STUDY: RISING CEA
ANTIBODY INFORMATION
ANTIBODY: Anti-CEA Whole IgG from Dr. HANSEN
BEFORE LABELING
Protein:   0.0 mg/ml    Method:
LABELING
Date: 12/23/83       Time:       Isotope: I-125
Activity added:         0.00 mCi
Concentration:
AFTER LABELING
% BOUND: 0.0%
Isotope Removal Method:
Protein:   0.0 mg/ml    Method:
Affinity:                        Method:
INJECTION
Date: 12/23/83      Time: 10:00
Activity:    0.00 mCi      VOLUME: 0.0 mls SURGERY
Date: 12/30/83       Time: 10:15
Operation: LEFT LIVER RESECTION
Findings: EXTENSIVE LEFT LIVER METASTASIS
Histological Report:LIVER-ADENOCARCINOMA
PROBE
Model: MODEL 4
Counting Duration:       20 sec   Collimation:
Surgical approach was not altered by probe use.
Comments: FIRST USE OF I-125 ISOTOPE EXCLUSIVELY

PATIENT NAME: J P
PROBE COUNTS

| TISSUE | AP/PA/C—C | INVIVO/INVITRO | MEAN COUNT |
|---|---|---|---|
| ROOM BACKGROUND | | | 0.00 |
| LEFT LIVER-B1 | AP | IN | 19.33 |
| LIVER TUMOR-T1 | AP | IN | 50.67 |
| LEFT LIVER-(B2) | AP | EX | 49.33 |
| LIVER TUMOR-(T2) | AP | EX | 10.00 |
| STOMACH | AP | IN | 18.00 |
| SPLEEN | AP | IN | 6.00 |
| COLON | AP | IN | 8.50 |

Tumor/Background Ratio:
1 - 2.62
(2) - 0.20

NEOPROBE HUMAN STUDIES - CLINICAL DATA REPORT
09/05/86
PATIENT NAME: C M          HOSPITAL NUMBER: 900-73-4019
PRESENT STATUS AS OF 09/01/86: ALIVE WITH CANCER
DISEASE CATEGORY: Rectal CA

DIAGNOSTIC IMAGING

| DATE | SCAN | P/N | INTERPRETATION OF SCAN | CORRELATION |
|---|---|---|---|---|
| 04/10/85 | COLONSCOPY | P | MASS IN RECTUM | TP |
| 05/13/85 | CHEST X-RAY | N | | |
| 11/30/85 | CAT - ABDOMINAL | P | LIVER METS. | TP |
| 12/03/85 | NMR - MRI | P | MASS ANTERIOR TO COCCYX | TP |
| 12/12/85 | BONE SCAN | N | | TN |
| 12/16/85 | CHEST X-RAY | P | 2 METS. NODES IN R LUNG | |

TABLE A-continued

12/18/85 CAT - CHEST     N     CALCIFIED NODE IN R LUNG
Index damaged. REINDEX should be done before using data.
LAB TESTS
DATE    TEST                             RESULTS SURGICAL HISTORY
DATE    PROCEDURE                          PROBE USED
05/13/85   A-P RESECTION                    Y
12/20/85   L LATERAL SEGMENTECTOMY      Y
PATIENT NAME: C M
DETAILED INFORMATION FOR SURGERY DATE: 05/13/85
REASON FOR STUDY: MASS IN RECTUM
ANTIBODY INFORMATION
ANTIBODY: 17-1A Whole IgG from CENTOCOR
BEFORE LABELING
Protein:    0.0 mg/ml    Method:
LABELING
Date: 05/09/85     Time:     Isotope: I-125
Activity added:        0.00 mCi
Concentration
AFTER LABELING
% BOUND: 0.0%
Isotope Removal Method:
Protein:    0.0 mg/ml    Method:
Affinity:                        Method:
INJECTION
Date: 05/09/85     Time: 12:30
Activity:    3.00 mCi     VOLUME: 0.0 mls SURGERY
Date: 05/13/85     Time: 12:10
Operation: A-P RESECTION
Findings: LARGE RECTAL MASS
Histological Report:RECTUM & LYMPH NODES-ADENOCARCINOMA
PROBE
Model: MODEL 7, LEAD PROBE
Counting Duration:           20 sec    Collimation:    0
Surgical approach was not altered by probe use.
Comments: TUMOR COUNTS WERE HIGHER THAN NORMAL TISSUE

PATIENT NAME: C M
PROBE COUNTS

| TISSUE | AP/PA/C—C | INVIVO/INVITRO | MEAN COUNT |
|---|---|---|---|
| AORTA | AP | IN | 18.00 |
| L LATERAL PELVIS | AP | IN | 7.00 |
| R LATERAL PELVIS | AP | IN | 13.00 |
| PELVIS-DEEP | AP | IN | 21.00 |
| PELVIS | AP | IN | 12.00 |
| TUMOR BED | AP | IN | 12.00 |
| BLADDER | AP | IN | 13.00 |
| ABD WALL | AP | IN | 9.50 |
| R LIVER | AP | IN | 24.00 |
| L LIVER | AP | IN | 29.00 |
| SPLEEN | AP | IN | 6.00 |
| STOMACH | AP | IN | 34.50 |
| SM BOWEL | AP | IN | 12.00 |
| RECTAL TUMOR-T1 | AP | EX | 12.00 |
| COLON-B1 | AP | EX | 12.00 |
| COLON-NODE | AP | EX | 4.00 |
| COLON-(B2) | AP | IN | 12.00 |
| RECTAL TUMOR-(T2) | AP | IN | 21.00 |

Tumor/Background Ratio:
1 - 1.00
(2) - 1.75

NEOPROBE HUMAN STUDIES - CLINICAL DATA REPORT
09/05/86
PATIENT NAME: T B        HOSPITAL NUMBER: 900-25-8500
PRESENT STAUS AS OF 09/01/86: ALIVE WITHOUT CA
DISEASE CATEGORY: Rectal CA DIAGNOSTIC IMAGING
DATE     SCAN           P/N   INTERPRETATION OF SCAN        CORRELATION
04/17/85   BONE SCAN         N
05/05/85   CAT - ABDOMINAL   P    TUMOR IN PELVIS & NODES      TP
05/06/85   ANTIBODY           P    TUMOR IMAGED                  TP
Index damaged. REINDEX should be done before using data.
LAB TESTS
DATE    TEST                             RESULTS

SURGICAL HISTORY

TABLE A-continued

| DATE | PROCEDURE | PROBE USED |
|---|---|---|
| 01/06/86 | RELEASE OF SM BOWEL OBSTRUCTION | Y |
| 04/28/86 | PERINEAL EXPLORATION | Y |
| 05/06/85 | SMALL BOWEL RESECTION, BX OF LYMPH NODES | Y |
| 05/06/86 | TRANSACRAL EXPLORATION | Y |
| 07/21/86 | EXP LAB | Y |
| 08/08/84 | A-P RESECTION | N |

PATIENT NAME: T B
DETAILED INFORMATION FOR SURGERY DATE: 05/06/85
REASON FOR STUDY: RISING CEA, TUMOR IN PELVIS
ANTIBODY INFORMATION
ANTIBODY: 17-1A Whole IgG from CENTOCOR
BEFORE LABELING
Protein   0.0 mg/ml   Method:
LABELING
Date: 05/03/85   Time:   Isotope: I-131
Activity added:   0.00 mCi
Concentration:
AFTER LABELING
% BOUND: 0.0%
Isotope Removal Method:
Protein:   0.0 mg/ml   Method:
Affinity:   Method:
INJECTION
Date: 05/03/86   Time: 12:40
Activity:   1.90 mCi   VOLUME: 0.0 mls SURGERY
Date: 05/06/85   Time: 15:42
Operation: SMALL BOWEL RESECTION, BX OF LYMPH NODES
Findings: TUMOR AT ANASTAMOSIS SITE & ADHERED TO PELVIS
Histological Report:MESENTERIC TISSUE-ADENOCARCINOMA
PROBE
Model: MODEL 7, LEAD PROBE
Counting Duration:   20 sec   Collimation:   0
Surgical approach was not altered by probe use.
Comments: HIGH BLOOD BACKGROUND COUNTS

PATIENT NAME: T B
PROBE COUNTS

| DATE | AP/PA/C—C | INVIVO/INVITRO | MEAN COUNT |
|---|---|---|---|
| AORTA | AP | IN | 53.00 |
| PARA-AORTIC NODE | AP | IN | 65.00 |
| BIF. OF AORTA | AP | IN | 123.00 |
| L. ILIAC | AP | IN | 30.00 |
| R ILIAC | AP | IN | 41.00 |
| PELVIC WALL | AP | IN | 17.00 |
| DEEP IN PELVIS | AP | IN | 23.00 |
| L INT. ILIAC | AP | IN | 34.00 |
| BIF EX. INT. ILIAC | AP | IN | 29.00 |
| MESENTERY-B1 | AP | IN | 30.00 |
| PERIAORTIC LYM. NODE | AP | IN | 15.00 |
| L. ILIAC | AP | IN | 65.00 |
| L.ILIAC | AP | IN | 47.00 |
| L PROX. ILIAC NODE | AP | IN | 15.50 |
| BETWEEN COMMON ILIAC | AP | IN | 47.00 |
| MESENTERIC MASS-T1 | AP | | 47.33 |

Tumor/Background Ratio:
1 - 1.58

NEOPROBE HUMAN STUDIES - CLINICAL DATA REPORT
09/05/86
PATIENT NAME: M P   HOSPITAL NUMBER: 900-29-0452
PRESENT STAUS AS OF 09/01/86: ALIVE WITH CA
DISEASE CATEGORY: R Colon/Transverse CA

DIAGNOSTIC IMAGING

| DATE | SCAN | P/N | INTERPRETATION OF SCAN | CORRELATION |
|---|---|---|---|---|
| 05/29/85 | CAT - ABDOMINAL | P | PELVIC MASS | TP |
| 05/29/85 | CHEST X-RAY | P | LUNG BIOPSY-FIBROSIS | FP |
| 05/29/85 | COLONSCOPY | N | | TN |
| 05/29/85 | BONE SCAN | N | | |
| 06/10/85 | ANTIBODY | N | NO TUMOR IMAGED | FN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 06/17/85 | EXP LAP, BX OF PELVIC WALL | Y |

TABLE A-continued

PATIENT NAME: M P
DETAILED INFORMATION FOR SURGERY DATE: 06/17/85
REASON FOR STUDY: RISING CEA, PELVIC MASS
ANTIBODY INFORMATION
ANTIBODY: 17-1A Whole IgG from CENTOCOR
BEFORE LABELING
Protein: 0.0 mg/ml    Method:
LABELING
Date: 06/07/85    Time:    Isotope: I-131
Activity added:    0.00 mCi
Concentration:
AFTER LABELING
% BOUND: 0.0%
Isotope Removal Method:
Protein: 0.0 mg/ml    Method:
Affinity:    Method:
INJECTION
Date: 06/07/85    Time: 12:30
Activity:    3.30 mCi    VOLUME: 0.0 mls SURGERY
Date: 06/17/85    Time: 07:30
Operation: EXP LAP, BX OF PELVIC WALL
Findings: EXTENSIVE LIVER & PELVIC METASTASES
Histological Report: SOFT TISSUE, PELVIC SIDEWALL-ADENOCARCINOMA
PROBE
Model: MODEL 7, LEAD PROBE
Counting Duration:    20 sec    Collimation:
Surgical approach was not altered by probe use.
Comments: BLOOD BACKGROUND COUNTS HIGHER THAN TUMOR

PATIENT NAME: M P
PROBE COUNTS

| TISSUE | AP/PA/C—C | INVIVO/INVITRO | MEAN COUNT |
|---|---|---|---|
| AORTA | AP | IN | 31.00 |
| LIVER TUMOR-T1 | AP | IN | 22.00 |
| LIVER-B1 | AP | IN | 7.00 |
| PELVIC TUMOR-(T2) | AP | IN | 19.00 |
| PELVIC WALL-(B2) | AP | IN | 8.00 |
| STOMACH | AP | IN | 75.00 |
| SPLEEN | AP | IN | 31.00 |
| COLON | AP | IN | 26.00 |
| SM BOWEL | AP | IN | 14.00 |

Tumor/Background Ratio:
1 - 3.14
(2) - 2.38

NEOPROBE HUMAN STUDIES - CLINICAL DATA REPORT
PATIENT NAME: V K    HOSPITAL NUMBER: 900-29-1137
PRESENT STATUS AS OF 09/01: ALIVE WITHOUT CA
DISEASE CATEGORY: Rectal CA

DIAGNOSTIC IMAGING

| DATE | SCAN | P/N | INTERPRETATION OF SCAN | CORRELATION |
|---|---|---|---|---|
| 05/20/86 | CHEST X-RAY | N | | |
| 06/06/85 | COLONOSCOPY | P | MASS IN RECTUM | TP |
| 06/10/85 | ANTIBODY | N | NO TUMOR IMAGED | FN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 05/16/86 | CLOSURE OF COLOSTOMY | Y |
| 06/10/85 | SIGMOID RESECTION | Y |

PATIENT NAME: V K
DETAILED INFORMATION FOR SURGERY DATE: 06/10/85
REASON FOR STUDY: MASS IN COLON
ANTIBODY INFORMATION
ANTIBODY: 17-1A Whole IgG from CENTOCOR
BEFORE LABELING
Protein: 0.0 mg/ml    Method:
LABELING
Date: 06/07/85    Time:    Isotope: I-131
Activity added:    0.00 mCi
Concentration:
AFTER LABELING
% BOUND: 0.0%
Isotope Removal Method:
Protein: 0.0 mg/ml    Method:
Affinity:    Method:

TABLE A-continued

INJECTION
Date: 06/07/85   Time: 13:00
Activity:   3.30 mCi   VOLUME: 0.0 mls

SURGERY
Date: 06/10/85   Time: 10:15
Operation: SIGMOID RESECTION
Findings: TUMOR CONFINED TO COLON
Histological Report: COLON & MESENTERY FAT-ADENOCARCINOMA
PROBE
Model: MODEL 7, LEAD PROBE
Counting Duration:   0 sec   Collimation   0
Surgical approach was not altered by probe use.
Comments: TUMOR COUNTS HIGHER THAN NORMAL TISSUE

PATIENT NAME: V K
PROBE COUNTS

| TISSUE | AP/PA/C—C | INVIVO/INVITRO | MEAN COUNT |
|---|---|---|---|
| AORTA | AP | IN | 61.00 |
| L LIVER | AP | IN | 83.00 |
| R LIVER | AP | IN | 28.00 |
| COLON TUMOR-T1 | AP | IN | 55.67 |
| COLON-B1 | AP | IN | 21.00 |
| PELVIS | AP | IN | 28.00 |

Tumor/Background Ratio:
1 - 2.65

NEOPROBE HUMAN STUDIES - CLINICAL DATA REPORT
09/05/86
PATIENT NAME: J R   HOSPITAL NUMBER: 300-30-2459
PRESENT STATUS AS OF 09/01/86: ALIVE WITH CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 08/06/85 | LEFT COLON RESECTION | Y |

PATIENT NAME: J R
DETAILED INFORMATION FOR SURGERY DATE: 08/06/85
REASON FOR STUDY: MASS IN COLON
ANTIBODY INFORMATION
ANTIBODY: Anti-CEA Whole IgG from DR. HAAG
BEFORE LABELING
Protein:   0.0 mg/ml   Method:
LABELING
Date: 08/02/85   Time:   Isotope: I-125
Activity added:   0.00 mCi
Concentration:
AFTER LABELING
% BOUND: 0.0%
Isotope Removal Method:
Protein:   0.0 mg/ml   Method:
Affinity:   Method:
INJECTION
Date: 08/02/85   Time: 12:00
Activity:   2.77 mCi   VOLUME: 0.0 mls SURGERY
Date: 08/06/85   Time: 08:15
Operation: LEFT COLON RESECTION
Findings: TUMOR CONFINED TO COLON
Histological Report: COLON MASS-ADENOCARCINOMA
PROBE
Model: MODEL 7, LEAD PROBE
Counting Duration:   20 sec   Collimation:
Surgical approach was not altered by probe use.
Comments: COULD HAVE DEFINED AREA OF RESECTION

PATIENT NAME: J R
PROBE COUNTS

| TISSUE | AP/PA/C—C | INVIVO/INVITRO | MEAN COUNT |
|---|---|---|---|
| AORTA | AP | IN | 55.00 |
| COLON TUMOR-T1 | AP | IN | 76.00 |
| COLON-B1 | AP | IN | 35.00 |
| TUMOR BED | AP | IN | 32.33 |

TABLE A-continued

| | | | |
|---|---|---|---|
| R PELVIC WALL | AP | IN | 30.00 |
| LIVER | AP | IN | 73.50 |
| COLON TUMOR-(T2) | AP | EX | 47.00 |
| COLON-(B2) | AP | EX | 21.50 |

Tumor/Background Ratio:
1 - 2.17
2 - 2.19

NEOPROBE HUMAN STUDIES - CLINICAL DATA REPORT
09/05/86
PATIENT NAME: O H   HOSPITAL NUMBER: 900-30-1219
PRESENT STATUS AS OF 09/01/86: ALIVE WITHOUT CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 10/11/85 | BARIUM ENEMA | P | SIGMOID MASS | TP |
| 11/03/85 | COLONOSCOPY | P | | TP |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 11/06/85 | L COLON RESECTION, PVC | Y |

PATIENT NAME: O H
DETAILED INFORMATION FOR SURGERY DATE: 11/06/85
REASON FOR STUDY: PRIMARY COLON CA
ANTIBODY INFORMATION
ANTIBODY: 17-1A F(ab')2 from CENTOCOR
BEFORE LABELING
Protein:   0.3 mg/ml   Method:
LABELING
Date: 11/04/85   Time: 09:30   Isotope: I-125
Activity added:   2.70 mCi
Concentration: 9.02 mCi/mg
AFTER LABELING
% BOUND: 87.0%
Isotope Removal Method: SEPHADEX COL. & CENTRICON-10
Protein:   0.3 mg/ml   Method:
Affinity:           Method:
INJECTION
Date: 11/04/85   Time: 17:30
Activity:   2.50 mCi   VOLUME: 2.0 mls SURGERY
Date: 11/06/85   Time: 08:18
Operation: L COLON RESECTION, PVC
Findings: COLON TUMOR WITH METASTASIS TO MESENTERIC NODE
Histological Report: COLON TUMOR & NODE-ADENOCARCINOMA
PROBE
Model: MODEL 7, LEAD PROBE
Counting Duration:   20 sec   Collimation: 0 mm
Surgical approach was altered by probe use.
Comments: AREA OF RESECTION WAS EXTENDED TO INCLUDE NODE

PATIENT NAME: O H
PROBE COUNTS

| TISSUE | AP/PA/C-C | INVIVO/INVITRO | MEAN COUNT |
|---|---|---|---|
| AORTA | AP | IN | 96.00 |
| STOMACH | AP | IN | 348.00 |
| TRANS. COLON-B1 | AP | IN | 46.67 |
| SM. BOWEL | AP | IN | 77.00 |
| COLON TUMOR-T1 | AP | IN | 139.33 |
| MESENTERIC NODE | AP | IN | 120.00 |
| R. LIVER | AP | IN | 138.00 |
| R. LIVER | PA | IN | 46.00 |
| L. LIVER | AP | IN | 148.00 |
| L. LIVER | PA | IN | 94.00 |
| ABD. WALL | AP | IN | 37.00 |
| COLON TUMOR-(T2) | AP | EX | 121.00 |
| COLON-(B2) | AP | EX | 22.00 |
| MESENTERY-(B3) | AP | EX | 6.00 |
| MESENTERIC NODE-((T3)) | AP | EX | 39.33 |
| ROOM BACKGROUND | | | 1.00 |

Tumor/Background Ratio:
1 - 2.99
(2) - 5.50
((3)) - 6.56
4 - * * ERROR: Unable to find tumor(-T4) and/or background(-B4)

TABLE A-continued

NEOPROBE HUMAN STUDIES - CLINICAL DATA REPORT
09/05/86
PATIENT NAME: A W　　　　HOSPITAL NUMBER: 900-24-8981
PRESENT STATUS AS OF 09/01/86: ALIVE WITHOUT CA
DISEASE CATEGORY: R Colon/Transverse CA

DIAGNOSTIC IMAGING

| DATE | SCAN | P/N | INTERPRETATION OF SCAN | CORRELATION |
|---|---|---|---|---|
| 01/11/86 | COLONOSCOPY | N | | TN |
| 01/11/86 | ARTERIOGRAM | N | | FN |
| 01/11/86 | BONE SCAN | N | | TN |
| 01/11/86 | CHEST X-RAY | N | | |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 02/02/86 | EXCISION OF MESENTERIC NODE & LIVER MASSES X 2 | Y |

PATIENT NAME: A W
DETAILED INFORMATION FOR SURGERY DATE: 02/02/86
REASON FOR STUDY: RISING CEA
ANTIBODY INFORMATION
ANTIBODY: 17-1A F(ab')2 from CENTOCOR
BEFORE LABELING
Protein:　1.0 mg/ml　Method: LOWERY
LABELING
Date: 01/29/86　　　Time: 10:30　　　Isotope: I-125
Activity added:　　　5.10 mCi
Concentration: 4.5 mCi/mg
AFTER LABELING
% BOUND: 95.0%
Isotope Removal Method: SEPHADEX COL.
Protein:　0.6 mg/ml　Method: LOWERY
Affinity:　　　　　　　　　　Method:
INJECTION
Date: 01/29/86　　　Time: 19:05
Activity:　4.50 mCi　　VOLUME: 1.8 mls SURGERY
Date: 02/02/86　　　Time: 11:38
Operation: EXCISION OF MESENTERIC NODE & LIVER MASSES X 2
Findings: TUMOR CONFINED TO MESENTERIC NODE AND LIVER
Histological Report: LIVER MASSES & MESENTERIC NODE-ADENOCARCINOMA
PROBE
Model: MODEL 9, 1 cm CRYSTAL
Counting Duration:　　　5 sec　Collimation: 2 mm
Surgical approach was altered by probe use.
Comments: PROBE DIRECTED EXCISION OF MESENTERIC NODE

PATIENT NAME: A W
PROBE COUNTS

| TISSUE | AP/PA/C—C | INVIVO/INVITRO | MEAN COUNT |
|---|---|---|---|
| AORTA | AP | IN | 84.00 |
| VENA CAVA | AP | IN | 53.00 |
| ABD. WALL | AP | IN | 39.50 |
| COLON | AP | IN | 84.00 |
| COLON | CC | IN | 74.00 |
| BLADDER | AP | IN | 79.00 |
| KIDNEY | AP | IN | 161.00 |
| R. LIVER | AP | IN | 82.33 |
| L. LIVER-B1 | AP | IN | 83.00 |
| PELVIS | AP | IN | 45.00 |
| SM. BOWEL | AP | IN | 58.00 |
| STOMACH, E-G | AP | IN | 111.00 |
| STOMACH, MID | AP | IN | 157.00 |
| STOMACH, ANTRUM | AP | IN | 104.00 |
| MESENTERIC TUMOR-(T2) | AP | IN | 84.67 |
| MESENTERIC TUMOR | PA | IN | 111.00 |
| L. LIVER TUMOR-T1 | AP | IN | 120.67 |
| COLON-ANATAMOSIS | AP | IN | 89.00 |
| MESEN.TUMOR IN OR | AP | EX | 19.00 |
| L LIVER TUMOR IN OR | AP | EX | 67.00 |
| R. LIVER TUMOR IN OR | AP | EX | 78.00 |
| ROOM BACKGROUND | | | 71.00 |
| L LIVER TUMOR((T3)) | AP | EX | 51.00 |
| R LIVER TUMOR- T4 | AP | EX | 52.33 |
| L LIVER((B3)) | AP | EX | 13.67 |
| LIVER- B4 | AP | EX | 13.67 |
| SM BOWEL MES-(B2) | AP | EX | 49.00 |

TABLE A-continued

Tumor/Background Ratio:
1 - 1.45
(2) - 1.73
((3)) - 3.73
 4 - 3.83

NEOPROBE HUMAN STUDIES - CLINICAL DATA REPORT
09/05/86
PATIENT NAME: K G   HOSPITAL NUMBER: 900-25-3152
PRESENT STATUS AS OF 09/01/86: ALIVE WITHOUT CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 09/11/85 | CAT - ABDOMINAL | P | PELVIC MASS | TP |
| 09/11/85 | NMR - MRI | P | PELVIC MASS | TP |

Index damaged. REINDEX should be done before using data.

LAB TESTS

| DATE | TEST | RESULTS |
|---|---|---|

SURGICAL HISTORY

| DATE | PROCEDURE | PROBE USED |
|---|---|---|
| 06/11/84 | L COLON RESECTION | N |
| 09/16/85 | EXCISION OF L GUTTER TUMOR & OOPHRECTOMY | Y |

PATIENT NAME: K G
DETAILED INFORMATION FOR SURGERY DATE: 09/16/85
REASON FOR STUDY: RISING CEA
ANTIBODY INFORMATION
ANTIBODY: 17-1A Whole IgG from DR. BARTH
BEFORE LABELING
Protein:    1.0 mg/ml    Method:
LABELING
Date: 09/11/85    Time:    Isotope: I-125
Activity added:    4.00 mCi
Concentration: 4.69 mCi/mg
AFTER LABELING
% BOUND: 0.0%
Isotope Removal Method: SEPHADEX COL
Protein:    0.0 mg/ml    Method:
Affinity:    Method:
INJECTION
Date: 09/11/85    Time: 14:00
Activity:    2.50 mCi    VOLUME: 0.0 mls SURGERY
Date: 09/16/85    Time: 07:30
Operation: EXCISION OF L GUTTER TUMOR & OOPHRECTOMY
Findings: METASTATIC COLON MASS IN L GUTTER
Histological Report: L GUTTER MASS-ADENOCARCINOMA
PROBE
Model: MODEL 7, LEAD PROBE
Counting Duration:    20 sec    Collimation: 0 mm
Surgical approach was altered by probe use.
Comments: PROBE DIRECTED EXCISION OF TUMOR BED

PATIENT NAME: K G
PROBE COUNTS

| TISSUE | AP/PA/C—C | INVIVO/INVITRO | MEAN COUNT |
|---|---|---|---|
| L GUTTER TUMOR-T1 | AP | IN | 272.00 |
| SUBCUTANEOUS FAT | AP | IN | 39.00 |
| LIVER | AP | IN | 159.00 |
| L GUTTER MUSCLE-B1 | AP | IN | 39.33 |
| RECTUM | PA | IN | 135.00 |
| AORTA | AP | IN | 84.00 |
| GALL BLADDER | AP | IN | 162.00 |
| OMENTUM | AP | IN | 145.00 |
| TUMOR BED-SUPERIOR 1 | AP | IN | 72.00 |
| TUMOR BED-SUPERIOR 2 | AP | IN | 24.00 |
| TUMOR BED-LATERAL 1 | AP | IN | 63.00 |
| TUMOR BED-LATERAL 2 | AP | IN | 51.00 |
| TUMOR BED-LATERAL 3 | AP | IN | 42.00 |
| TUMOR BED-INFERIOR | AP | IN | 43.00 |
| TUMOR BED-SUPERIOR | AP | EX | 72.00 |
| TUMOR BED-LATERAL 1 | AP | EX | 9.00 |
| TUMOR BED-LATERAL 2 | AP | EX | 25.00 |
| TUMOR BED-MEDIAL | AP | IN | 55.00 |
| TUMOR BED-MEDIAL | AP | EX | 26.00 |
| L GUTTER TUMOR-(T2) | AP | EX | 190.67 |
| L GUTTER MUSCLE-(B2) | AP | EX | 30.00 |
| L OVARY | AP | IN | 157.00 |
| L OVARY | AP | EX | 47.00 |

TABLE A-continued

Tumor/Background Ratio:
1 - 6.92
(2) - 6.36

NEOPROBE HUMAN STUDIES - CLINICAL DATA REPORT
09/05/86
PATIENT NAME: L B           HOSPITAL NUMBER: 900-30-0446
PRESENT STATUS AS OF 09/01/86: ALIVE WITHOUT CA
DISEASE CATEGORY: Small Bowel

DIAGNOSTIC IMAGING

| DATE | SCAN | P/N | INTERPRETATION OF SCAN | CORRELATION |
|---|---|---|---|---|
| 09/12/85 | LIVER/SPLEEN | N | | TN |
| 10/02/85 | CHEST X-RAY | N | | |
| 10/28/85 | NMR - MRI | N | | TN |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 06/11/85 | SMALL BOWEL RESECTION | N |
| 10/28/85 | R COLON RESECTION | Y |
| 10/28/85 | R COLON RESECTION | Y |

PATIENT NAME: L B
DETAILED INFORMATION FOR SURGERY DATE: 10/28/85
REASON FOR STUDY: RISING CEA
ANTIBODY INFORMATION
ANTIBODY: 17-1A Whole IgG from CENTOCOR
BEFORE LABELING
Protein:   0.2 mg/ml    Method: LOWERY
LABELING
Date: 10/24/85       Time: 09:00        Isotope: I-125
Activity added:         3.19 mCi
Concentration: 3.93 mCi/mG
AFTER LABELING
% BOUND: 0.0%
Isotope Removal Method: SEPHADEX COL
Protein:   0.0 mg/ml    Method:
Affinity:                          Method:
INJECTION
Date: 10/24/85       Time: 12:00
Activity:    2.15 mCi      VOLUME: 0.3 mls SURGERY
Date: 10/28/85       Time: 12:54
Operation: R COLON RESECTION
Findings: ENLARGED NODE, NO RECURRENT TUMOR
Histological Report: SMALL BOWEL-ADENOCARCINOMA
PROBE
Model: MODEL 7, LEAD PROBE
Counting Duration:         20 sec   Collimation:     0
Surgical approach was altered by probe use.
Comments: PROBE DIRECTED EXCISION SMALL BOWEL

PATIENT NAME: L B
PROBE COUNTS

| TISSUE | AP/PA/C—C | INVIVO/INVITRO | MEAN COUNT |
|---|---|---|---|
| AORTA | AP | IN | 37.50 |
| STOMACH | AP | IN | 60.00 |
| MESENTERIC NODE 1 | AP | IN | 16.00 |
| MESENTERIC NODE 2 | AP | IN | 20.00 |
| MESENTERIC NODE 3 | AP | IN | 13.00 |
| R PERICOLIC GUTTER | AP | IN | 20.00 |
| L COMMON ARTERY | AP | IN | 5.00 |
| ABD WALL | AP | IN | 9.00 |
| L LIVER | AP | IN | 23.00 |
| R LIVER | AP | IN | 19.00 |
| PORTA HEPATIS | AP | IN | 23.00 |
| KIDNEY | AP | IN | 11.00 |
| TRANSVERSE COLON | AP | IN | 27.00 |
| TRANSVERSE COLON | PA | IN | 10.00 |
| AORTA | AP | IN | 27.00 |
| MESENTERIC NODE 4 | AP | IN | 15.00 |
| SM BOWEL PROX. ANAST | AP | IN | 22.00 |
| SM BOWEL DIST. ANAST | AP | IN | 7.00 |
| SM BOWEL ANASTAMOSIS | AP | IN | 19.00 |
| MESENTERIC TUMOR-T1 | AP | IN | 31.00 |
| AORTIC LYMPH NODE | AP | IN | 22.00 |
| ROOM BACKGROUND | | | 6.00 |
| R SIDE OF AORTA | AP | IN | 18.00 |

TABLE A-continued

| | | | |
|---|---|---|---|
| MESENTERIC NODE 6 | AP | IN | 2.00 |
| MESENTERIC NODE 7 | AP | IN | 11.00 |
| MESENTERIC NODE 8 | AP | IN | 6.00 |
| MESENTERY-B1 | AP | IN | 16.00 |
| DEEP IN MESENTERY | AP | IN | 22.00 |
| MESENTERIC NODE 1 | AP | EX | 10.00 |
| MESENTERIC NODE 2 | AP | EX | 21.00 |

Tumor/Background Ratio:
1 - 1.94

NEOPROBE HUMAN STUDIES - CLINICAL DATA REPORT
09/05/86
PATIENT NAME: C R        HOSPITAL NUMBER: 900-25-1235
PRESENT STATUS AS OF 09/01/86: ALIVE WITH CA
DISEASE CATEGORY: Rectal CA

DIAGNOSTIC IMAGING

| DATE | SCAN | P/N | INTERPRETATION OF SCAN | CORRELATION |
|---|---|---|---|---|
| 08/30/85 | CAT - ABDOMINAL | P | MASS IN AREA OF MUCUS FISTULA | TP |
| 10/01/85 | NMR - MRI | N | | FN |
| 10/01/85 | CHEST X-RAY | N | | |

Index damaged. REINDEX should be done before using data.

LAB TESTS

| DATE | TEST | RESULTS |
|---|---|---|

SURGICAL HISTORY

| DATE | PROCEDURE | PROBE USED |
|---|---|---|
| 08/11/84 | A-P RESECTION | N |
| 10/07/85 | RESECTION OF PERINEAL FISTULA | Y |

PATIENT NAME: C R
DETAILED INFORMATION FOR SURGERY DATE: 10/07/85
REASON FOR STUDY: RISING CEA
ANTIBODY INFORMATION
ANTIBODY: 17-1A Whole IgG from DR. BARTH
BEFORE LABELING
Protein:    0.3 mg/ml    Method:
LABELING
Date: 10/01/85      Time:      Isotope: I-125
Activity added:         0.00 mCi
Concentration: 9.27 mCi/mg
AFTER LABELING
% BOUND: 0.0%
Isotope Removal Method: SEPHADEX COL
Protein:    0.0 mg/ml    Method:
Affinity:                     Method:
INJECTION
Date: 10/01/85      Time: 11:30
Activity:    2.00 mCi     VOLUME: 1.6 mls SURGERY
Date: 10/07/85      Time: 13:45
Operation: RESECTION OF PERINEAL FISTULA
Findings: NO TUMOR FOUND, PRELIMINARY PATH REPORT WAS NEG.
Histological Report: RECTUM-ADENOCARCINOMA
PROBE
Model: MODEL 7, LEAD PROBE
Counting Duration:          20 sec    Collimation:     0
Surgical approach was altered by probe use.
Comments: PROBE DIRECTED BX, FINAL PATH REPORT WAS CANCER

PATIENT NAME: C R
PROBE COUNTS

| TISSUE | AP/PA/C—C | INVIVO/INVITRO | MEAN COUNT |
|---|---|---|---|
| OMENTUM | AP | IN | 2.00 |
| SINUS TRACT LATERAL | AP | IN | 8.50 |
| SM BOWEL MESENTERY | AP | IN | 1.00 |
| LIVER | AP | IN | 17.00 |
| PELVIC FLOOR | AP | IN | 23.00 |
| DOME OF BLADDER | AP | IN | 26.00 |
| AORTA | AP | IN | 20.50 |
| STOMACH | AP | IN | 30.50 |
| COLON | AP | IN | 13.00 |
| PERIAORTIC L. NODE | AP | IN | 8.00 |
| PELVIC TUMOR-T1 | AP | IN | 34.67 |
| SINUS TRACT-B1 | AP | IN | 8.00 |
| COCCYX | AP | IN | 22.00 |
| SACRUM | AP | IN | 19.00 |
| PELVIC FIB. TISSUE | AP | IN | 28.00 |
| ROOM BACKGROUND | | | 1.00 |

Tumor/Background Ratio:

TABLE A-continued

1 - 4.33

NEOPROBE HUMAN STUDIES - CLINICAL DATA REPORT
09/05/86
PATIENT NAME: M S          HOSPITAL NUMBER: 900-30-2796
PRESENT STATUS AS OF 09/01/86: ALIVE WITHOUT CA
DISEASE CATEGORY: Rectal CA

DIAGNOSTIC IMAGING

| DATE | SCAN | P/N | INTERPRETATION OF SCAN | CORRELATION |
|---|---|---|---|---|
| 02/15/86 | NMR - MRI | P | SACRAL MASS | TP |
| 03/09/86 | CHEST X-RAY | N | | |
| 10/17/85 | BONE SCAN | P | MASS IN PELVIS | TP |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 03/11/86 | EXP LAP | Y |
| 03/18/86 | PERINEAL EXPLORATION | Y |
| 03/24/86 | PLACEMENT OF RADIATION CONE | Y |
| 11/26/83 | L COLON RESECTION | N |

PATIENT NAME: M S
DETAILED INFORMATION FOR SURGERY DATE: 03/11/86
REASON FOR STUDY: RECURRENT TUMOR IN PELVIS
ANTIBODY INFORMATION
ANTIBODY: B72.3 Whole IgG from NCI
BEFORE LABELING
Protein:    1.0 mg/ml    Method: LOWERY'S
LABELING
Date: 02/28/86         Time: 07:00         Isotope: I-125
Activity added:         6.00 mCi
Concentration: 6.68 mCi/mg
AFTER LABELING
% BOUND: 88.0%
Isotope Removal Method: SEPHADEX COL
Protein:    1.4 mg/ml    Method: LOWERY
Affinity:                              Method:
INJECTION
Date: 02/28/86         Time: 15:00
Activity:    4.40 mCi    VOLUME: 3.2 mls SURGERY
Date: 03/11/86         Time: 14:00
Operation: EXP LAP
Findings: RECURRENT COLON TUMOR IN PELVIS
Histological Report:
PROBE
Model: MODEL 9, 1 cm CRYSTAL
Counting Duration:        5 sec   Collimation: 0 mm
Surgical approach was altered by probe use.
Comments: SUSPECT TUMOR IN PELVIS

PATIENT NAME: M S
PROBE COUNTS

| TISSUE | AP/PA/C—C | INVIVO/INVITRO | MEAN COUNT |
|---|---|---|---|
| AORTA | AP | IN | 53.50 |
| ABD WALL | AP | IN | 14.00 |
| BLADDER | AP | IN | 144.00 |
| COLON | AP | IN | 17.00 |
| KIDNEY | AP | IN | 28.50 |
| R LIVER | AP | IN | 24.00 |
| L LIVER | AP | IN | 41.00 |
| PELVIS | AP | IN | 85.00 |
| SM BOWEL MESENTERY | AP | IN | 28.00 |
| STOMACH-E-G | AP | IN | 72.00 |
| STOMACH-MID | AP | IN | 62.00 |
| STOMACH-PYLORUS | AP | IN | 55.00 |
| SACRUM | AP | IN | 91.00 |
| PELVIC WALL-B1 | AP | IN | 71.00 |
| PELVIC TUMOR-T1 | AP | IN | 212.50 |
| ROOM BACKGROUND | | | 5.33 |

Tumor/Background Ratio:
1 - 2.99

PATIENT NAME: M S
PATHOLOGY
Diagnosis: SMALL BOWEL, MESENTERY & PELVIC MASS, FIBROSIS

| TISSUE | STAIN | WEIGHT (gms) | WELL COUNT (cpm) | CPM/GM |
|---|---|---|---|---|
| SMALL BOWEL | NEGATIVE | 0.000 | 0 | ******** |

TABLE A-continued

| | | | | |
|---|---|---|---|---|
| PELVIC MASS | NEGATIVE | 0.000 | 0 | ******** |

Antibody Localization: NEGATIVE
Preservation Method: PARAFFIN
Staining Method: ABC-IMP
Probe Use:

PATIENT NAME: M S
DETAILED INFORMATION FOR SURGERY DATE: 03/18/86
REASON FOR STUDY:
ANTIBODY INFORMATION

SURGERY
Date: 03/18/86    Time: 07:30
Operation: PERINEAL EXPLORATION
Findings: TUMOR LOCATED R LATERAL & MEDIAL ASPECT OF SACRUM
Histological Report: PELVIC SOFT TISSUE-ADENOCARCINOMA
PROBE
Model: MODEL 9, 1 cm CRYSTAL
Counting Duration:    5 sec    Collimation: 4 MM
Surgical approach was altered by probe use.
Comments: PROBE DIRECTED BX

PATIENT NAME: M S
PROBE COUNTS

| TISSUE | AP/PA/C—C | INVIVO/INVITRO | MEAN COUNT |
|---|---|---|---|
| L BUTTOCKS | AP | IN | 14.00 |
| R BUTTOCKS | AP | IN | 15.00 |
| L ISCH RECTAL FOSSA | AP | IN | 7.00 |
| R ISCH RECTAL FOSSA | AP | IN | 2.00 |
| R PRESACRUM | AP | IN | 49.00 |
| PROSTATE | AP | IN | 12.00 |
| COCCYX-B1 | AP | IN | 32.00 |
| COCCYX-SUPERIOR | AP | IN | 52.00 |
| HOLLOW OF SACRUM-T1 | AP | IN | 69.00 |
| PELVIC BX | AP | EX | 2.00 |
| ROOM BACKGROUND | | | 5.67 |

Tumor/Background Ratio:
1 - 2.16

PATIENT NAME: M S
PATHOLOGY
Diagnosis: SOFT TISSUE, PELVIS, ADENOCARCINOMA

| TISSUE | STAIN | WEIGHT (gms) | WELL COUNT (cpm) | CPM/GM |
|---|---|---|---|---|
| PELVIC TUMOR, Bx, B-AF | 3+, NEC,15% | 0.000 | 0 | ******** |
| PELVIC TUMOR, Bx, B-BF | 2+, NEC,40% | 0.000 | 0 | ******** |

Antibody Localization: NEGATIVE
Preservation Method: PARAFFIN
Staining Method: IMP-ABC
Probe Use:

PATIENT NAME: M S
DETAILED INFORMATION FOR SURGERY DATE: 03/24/86
REASON FOR STUDY:
ANTIBODY INFORMATION

SURGERY
Date: 03/24/86    Time:
Operation: PLACEMENT OF RADIATION CONE
Findings:
Histological Report: NO TISSUE SUBMITTED
PROBE
Model: MODEL 9, 1 cm CRYSTAL
Counting Duration:    5 sec    Collimation: 0 mm
Surgical approach was altered by probe use.
Comments: DIRECTED PLACEMENT OF CATHETERS FOR RADIATION RX

PATIENT NAME: M S
PROBE COUNTS

| TISSUE | AP/PA/C—C | INVIVO/INVITRO | MEAN COUNT |
|---|---|---|---|
| ROOM BACKGROUND | | | 6.33 |
| R ARM | AP | IN | 3.00 |
| THYROID | AP | IN | 231.00 |
| SKIN | AP | IN | 1.00 |
| SACRUM-MEDIAL-T1 | AP | IN | 71.33 |
| SACRUM-L LATERAL | AP | IN | 34.50 |
| SACRUM-R LATERAL | AP | IN | 73.50 |
| BASE OF COCCYX-B1 | AP | IN | 23.00 |

Tumor/Background Ratio:
1 - 3.10

TABLE A-continued

PATIENT NAME: R M  HOSPITAL NUMBER: 900-32-1492
PRESENT STATUS AS OF 09/01/86: ALIVE WITH CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 04/15/86 | CAT - ABDOMINAL | N | | |
| 04/18/86 | CHEST X-RAY | N | | |
| 04/18/86 | NMR - MRI | P | MASS IN SACRUM | TP |

Index damaged. REINDEX should be done before using data.

LAB TESTS

| DATE | TEST | RESULTS |
|---|---|---|

SURGICAL HISTORY

| DATE | PROCEDURE | PROBE USED |
|---|---|---|
| 04/19/86 | BX OF PELVIC MASS | Y |
| 09/08/84 | ANTERIOR COLON RESECTION | N |

PATIENT NAME: R M
DETAILED INFORMATION FOR SURGERY DATE: 04/19/86
REASON FOR STUDY: RISING CEA
ANTIBODY INFORMATION
ANTIBODY: B72.3 Whole IgG from NCI
BEFORE LABELING
Protein:  1.3 mg/ml  Method: LOWERY'S
LABELING
Date: 03/28/86  Time: 11:00  Isotope: I-125
Activity added:  5.70 mCi
Concentration: 4.838 mCi/mg
AFTER LABELING
% BOUND: 95.0%
Isotope Removal Method: SEPHADEX G-25 COL
Protein:  0.4 mg/ml  Method: LOWERY'S
Affinity:  Method:
INJECTION
Date: 03/28/86  Time: 13:00
Activity:  4.50 mCi  VOLUME: 2.0 mls SURGERY
Date: 04/19/86  Time: 08:10
Operation: BX OF PELVIC MASS
Findings: RECURRENT CA IN PELVIS
Histological Report: PELVIC TISSUE-MUCINOUS ADENOCARCINOMA
PROBE
Model: MODEL 9, 1 cm CRYSTAL
Counting Duration:  2 sec  Collimation: 0 mm
Surgical approach was altered by probe use.
Comments: PROBE DIRECTED BX OF PELVIC TUMOR

PATIENT NAME: R M
PROBE COUNTS

| TISSUE | AP/PA/C—C | INVIVO/INVITRO | MEAN COUNT |
|---|---|---|---|
| RM BACKGROUND | | | 3.00 |
| L BUTTOCKS | AP | OUT | 0.00 |
| TOWARD RECTUM | AP | IN | 12.00 |
| PELVIC TUMOR-T1 | AP | IN | 30.00 |
| R PELVIC WALL-B1 | AP | IN | 1.00 |
| DEEP IN PELVIS | AP | IN | 31.00 |
| DEEP IN PELVIS, LAT | AP | IN | 5.00 |
| DEEP IN PELVIS, MED | AP | IN | 13.00 |
| PELVIC BX #1 | AP | EX | 1.00 |
| PELVIC BX #2 | AP | EX | 2.00 |

Tumor/Background Ratio:
1 - 30.00

NEOPROBE HUMAN STUDIES - CLINICAL DATA REPORT
09/05/86
PATIENT NAME: J N  HOSPITAL NUMBER: 900-29-2533
PRESENT STATUS AS OF 08/21/86: ALIVE WITHOUT CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 06/03/86 | CHEST X-RAY | P | R LOBE MET | TP |
| 06/03/86 | CAT - ABDOMINAL | P | PRESACRAL MASS | TP |

Index damaged. REINDEX should be done before using data.

LAB TESTS

| DATE | TEST | RESULTS |
|---|---|---|

SURGICAL HISTORY

| DATE | PROCEDURE | PROBE USED |
|---|---|---|

TABLE A-continued

06/03/86 EXCISION OF LIVER AND PELVIC METS     Y
06/24/86 R UPPER LOBECETOMY, WEDGE RESECTION OF MID R LOBE     Y

PATIENT NAME: J N
DETAILED INFORMATION FOR SURGERY DATE: 06/03/86
REASON FOR STUDY: RISING CEA, MASS IN PRESACRAL
ANTIBODY INFORMATION
ANTIBODY: B72.3 Whole IgG from NCI
BEFORE LABELING
Protein:    1.3 mg/ml     Method: LOWERY'S
LABELING
Date: 05/21/86     Time: 01:45     Isotope: I-125
Activity added:     6.57 mCi
Concentration: 6.57 mCi/mg
AFTER LABELING
% BOUND: 95.0%
Isotope Removal Method: SEPHADEX G-25 COL
Protein:    1.0 mg/ml     Method: LOWERY'S
Affinity:                           Method:
INJECTION
Date: 05/21/86     Time: 16:45
Activity:    5.31 mCi     VOLUME 1.9 mls SURGERY
Date: 06/03/86     Time: 07:35
Operation: EXCISION OF LIVER AND PELVIC METS
Findings: TUMOR MASS IN LIVER, NO OTHER TUMOR FOUND
Histological Report: LIVER & RETROILIAC NODE-ADENOCARCINOMA
PROBE
Model: MODEL 9, 1 cm CRYSTAL
Counting Duration:          2 sec    Collimation: 0 mm
Surgical approach was altered by probe use.
Comments: PROBE DIRECTED FINDING OF RETROILIAC NODE

PATIENT NAME: J N
PROBE COUNTS

| TISSUE | AP/PA/C—C | INVIVO/INVITRO | MEAN COUNT |
|---|---|---|---|
| AORTA | AP | IN | 4.00 |
| VENA CAVA | AP | IN | 7.00 |
| ABD WALL | AP | IN | 3.00 |
| BLADDER | AP | IN | 93.00 |
| COLON | AP | IN | 5.00 |
| KIDNEY | AP | IN | 17.00 |
| R LIVER-B1 | AP | IN | 1.00 |
| L LIVER | AP | IN | 8.00 |
| SM BOWEL | AP | IN | 11.00 |
| SM BOWEL MESENTERY | AP | IN | 4.00 |
| STOMACH-E-G | AP | IN | 31.00 |
| STOMACH-MID | AP | IN | 21.00 |
| STOMACH-PYLORUS | AP | IN | 14.00 |
| OMENTUM | AP | IN | 6.00 |
| R LIVER TUMOR-T1 | AP | IN | 77.00 |
| R PELVIS, PRE-DIS. | AP | IN | 12.00 |
| L PELVIS, PRE-DIS. | AP | IN | 65.33 |
| L GROIN | AP | IN | 15.00 |
| L PELVIS p DIS #1 | AP | IN | 64.00 |
| ILIAC VEIN | AP | IN | 49.00 |
| TIS OFF IL.ART & VEI | AP | EX | 3.00 |
| L PELVIS p DIS #2 | AP | IN | 174.00 |
| RETROILIAC ARTERY | AP | EX | 7.00 |
| BEHIND ILIAC VEIN | AP | IN | 202.00 |
| RETRO ILIAC V LYMPAT | AP | EX | 5.00 |
| RETROILIAC NODE BED | AP | IN | 44.50 |
| 2 cm LATERAL TO BED | AP | IN | 11.00 |
| INFERIOR TO BED | AP | IN | 46.00 |
| LIVER TUMOR | AP | EX | 49.50 |
| LIVER TUMOR BED | AP | IN | 9.00 |
| AORTIC CHAIN | AP | IN | 20.00 |
| RENAL ARTERY | AP | IN | 14.00 |
| INFERIOR MES ARTERY | AP | IN | 12.00 |
| R ILIAC | AP | IN | 3.00 |
| PELVIC RIM | AP | IN | 8.00 |
| RETROILIAC NODE BED | AP | IN | 46.50 |
| SM BOWEL ADHESION | AP | IN | 6.00 |
| L ILIAC ARTERY & VEI | AP | IN | 15.00 |
| PROX TO RETROIL BED | AP | EX | 7.00 |
| L ILIAC NODE-(T2) | AP | IN | 202.00 |
| RETROILIAC NODE-(B2) | AP | IN | 64.00 |
| BACKGROUND | | | 7.00 |

Tumor/Background Ratio:
1 - 77.00
(2) - 3.16

TABLE A-continued

PATIENT NAME: J N
PATHOLOGY
Diagnosis:

| TISSUE | STAIN | WEIGHT (gms) | WELL COUNT (cpm) | CPM/GM |
|---|---|---|---|---|

Antibody Localization:
Preservation Method:
Staining Method:
Probe Use:

PATIENT NAME: J N
DETAILED INFORMATION FOR SURGERY DATE: 06/24/86
REASON FOR STUDY:
ANTIBODY INFORMATION

SURGERY
Date: 06/24/86  Time: 07:30
Operation: R UPPER LOBECETOMY, WEDGE RESECTION OF MID R LOBE
Findings: LG. MASS RUL, 1 cm MASS RML, .5 cm MASS RLL
Histological Report:
PROBE
Model: MODEL 9, 1 cm CRYSTAL
Counting Duration:  2 sec  Collimation: 0 mm t
Surgical approach was altered by probe use.
Comments: AREA OF RESECTION COULD HAVE BEEN EASILY DEFINED

PATIENT NAME: J N
PROBE COUNTS

| TISSUE | AP/PA/C—C | INVIVO/INVITRO | MEAN COUNT |
|---|---|---|---|
| LUNG-$B_1$ | AP | IN | 6.00 |
| SUBCU AROUND BREAST | AP | IN | 3.50 |
| DIAPHGRM | AP | IN | 1.50 |
| LUNG TUMOR-$T_1$ | AP | IN | 223.00 |
| ¼" AWAY FROM TUMOR | AP | IN | 9.00 |
| R MID LOBE MASS | AP | IN | 5.50 |
| MEDIASTINUM | AP | IN | 5.00 |
| R L LOBE MASS | AP | IN | 6.00 |
| POSTERIOR MEDIASTIN. | AP | IN | 2.00 |
| BACKGROUND | | | 5.67 |
| LUNG TUMOR-(T2) | AP | EX | 128.33 |
| R LUNG-(B2) | AP | EX | 6.00 |

Tumor/Background Ratio:
1 - 37.17
(2) - 21.39

NEOPROBE HUMAN STUDIES - CLINICAL DATA REPORT
09-05-86
PATIENT NAME: H K        HOSPITAL NUMBER: 900-02-7285
PRESENT STATUS AS OF 09/01/86: ALIVE WITHOUT CA
DISEASE CATEGORY: Breast CA

DIAGNOSTIC IMAGING

| DATE | SCAN | P/N | INTERPRETATION OF SCAN | CORRELATION |
|---|---|---|---|---|
| 06/22/86 | MAMMOGRAM | P | | TP |
| 06/25/86 | BONE SCAN | N | | TN |
| 06/25/86 | CHEST X-RAY | N | | |

Index damaged. REINDEX should be done before using data.
LAB TESTS

| DATE | TEST | RESULTS |
|---|---|---|

SURGICAL HISTORY

| DATE | PROCEDURE | PROBE USED |
|---|---|---|
| 07/07/86 | LEFT MASTECTOMY | Y |

PATIENT NAME: H K
DETAILED INFORMATION FOR SURGERY DATE: 07/07/86
REASON FOR STUDY: PRIMARY BREAST MASS, +CYTOLOGY
ANTIBODY INFORMATION
ANTIBODY: B72.3 Whole IgG from NCI
BEFORE LABELING
Protein:  1.8 mg/ml   Method: LOWERY'S
LABELING
Date: 06/25/86   Time: 09:30   Isotope: I-125
Activity added:  6.10 mCi
Concentration: 4.192 mCi/mg
AFTER LABELING
% BOUND: 91.0%
Isotope Removal Method: SEPHADEX G-25 COL
Protein:  0.4 mg/ml   Method: LOWERY'S
Affinity:           Method:
INJECTION

TABLE A-continued

Date: 06/25/86  Time: 13:30
Activity:  4.11 mCi   VOLUME: 2.4 mls

SURGERY
Date: 07/07/86  Time: 14:23
Operation: LEFT MASTECTOMY
Findings: NO VISIBLE OR PALPABLE TUMOR
Histological Report: LEFT BREAST-INVASIVE DUCTAL CARCINOMA
PROBE
Model: MODEL 9, 1 cm CRYSTAL
Counting Duration:   2 sec   Collimation: 0 mm
Surgical approach was altered by probe use.
Comments: PROBE DIRECTED BX OF BREAST TO ESTABLISH DIAGNOSIS

PATIENT NAME: H K
PROBE COUNTS

| TISSUE | AP/PA/C—C | INVIVO/INVITRO | MEAN COUNT |
|---|---|---|---|
| LEFT BREAST MASS | AP | OUT | 49.00 |
| BACKGROUND | | | 4.33 |
| L BREAST | AP | OUT | 152.00 |
| R BREAST | AP | OUT | 141.00 |
| STERNUM | AP | OUT | 136.00 |
| ABDOMEN | AP | OUT | 103.00 |
| L ARM | AP | OUT | 34.00 |
| L CHEST WALL | AP | OUT | 190.00 |
| L BREAST BED | AP | OUT | 18.00 |
| AXILLARY AREA TO ARM | AP | IN | 41.00 |
| AXILLARY AREA, HEAD | AP | IN | 52.00 |
| AXILLARY NODE #1 | AP | IN | 65.50 |
| AXILLARY NODE #2 | AP | IN | 16.00 |
| AXILLARY NODE #1 | AP | EX | 10.00 |
| AXILLA | AP | IN | 83.00 |
| L BREAST MASS BX | AP | EX | 35.00 |
| L BREAST TUMOR-T1 | AP | EX | 53.00 |
| L BREAST TISSUE-B1 | AP | EX | 13.00 |
| AXILLARY AREA | AP | EX | 13.67 |
| L ARM | AP | OUT | 62.00 |
| L CALF | AP | OUT | 49.00 |
| R BREAST | AP | OUT | 114.67 |
| L BREAST | AP | OUT | 118.67 |

Tumor/Background Ratio:
1 - 4.08

NEOPROBE HUMAN STUDIES - CLINICAL DATA REPORT
09/05/86
PATIENT NAME: E W          HOSPITAL NUMBER: 163-73-7000
PRESENT STATUS AS OF 09/01/86: ALIVE WITH CA
DISEASE CATEGORY: L Colon/Sigmoid CA

DIAGNOSTIC IMAGING

| DATE | SCAN | P/N | INTERPRETATION OF SCAN | CORRELATION |
|---|---|---|---|---|
| 02/02/86 | COLONOSCOPY | P | SUTURE LINE RECURRENCE | TP |
| 02/06/86 | CHEST X-RAY | N | | |
| 02/07/86 | CAT - ABDOMINAL | N | | FN |
| 07/07/86 | CHEST X-RAY | P | NODE R LOWER LUNG | |

Index damaged. REINDEX should be done before using data.
LAB TESTS
DATE   TEST                              RESULTS

SURGICAL HISTORY

| DATE | PROCEDURE | PROBE USED |
|---|---|---|
| 02/10/86 | HARTMAN POUCH | Y |
| 07/10/86 | EXP LAP, HAL | Y |

PATIENT NAME: E W
DETAILED INFORMATION FOR SURGERY DATE: 07/10/86
REASON FOR STUDY: METS TO LIVER
ANTIBODY INFORMATION
ANTIBODY: 17-1A Whole IgG from CENTOCOR
BEFORE LABELING
Protein:  0.0 mg/ml   Method:
LABELING
Date: 06/30/86      Time:       Isotope: I-125
Activity added:      0.00 mCi
Concentration:
AFTER LABELING
% BOUND: 0.0%
Isotope Removal Method:
Protein:  0.0 mg/ml   Method:
Affinity:                    Method:
INJECTION
Date: 06/30/86      Time:

TABLE A-continued

Activity: 0.00 mCi  VOLUME: 0.0 mls

SURGERY
Date: 07/10/86  Time: 09:01
Operation: EXP LAP, HAL
Findings: MULTIPLE METASTATIC LIVER TUMORS
Histological Report:
PROBE
Model: MODEL 9, 1 cm CRYSTAL
Counting Duration:  2 sec  Collimation: 0 mm
Surgical approach was not altered by probe use.
Comments: GOOD LIVER TUMOR: TISSUE DIFFERENTIATION

PATIENT NAME: E W
PROBE COUNTS

| TISSUE | AP/PA/C—C | INVIVO/INVITRO | MEAN COUNT |
|---|---|---|---|
| AORTA | AP | IN | 8.00 |
| VENA CAVA | AP | IN | 6.00 |
| ABD WALL | AP | IN | 10.00 |
| BLADDER | AP | IN | 9.00 |
| COLON | AP | IN | 7.00 |
| KIDNEY | AP | IN | 9.00 |
| R LIVER-B1 | AP | IN | 15.00 |
| L LIVER | AP | IN | 12.00 |
| SM BOWEL | AP | IN | 7.00 |
| SM BOWEL MESENTERY | AP | IN | 5.00 |
| STOMACH-E-G | AP | IN | 10.00 |
| STOMACH-MID | AP | IN | 5.00 |
| STOMACH-PYLORUS | AP | IN | 16.00 |
| R LIVER TUMOR-T1 | AP | IN | 111.00 |
| DOME OF LIVER | AP | IN | 33.50 |
| DOME L LOBE-(B2) | AP | IN | 58.50 |
| L LOBE DOME NODE-(T2) | AP | IN | 57.50 |
| R TUMOR p HAL | AP | IN | 159.00 |
| L LATERAL SEGMENT | AP | IN | 83.33 |
| MID PELVIS | AP | IN | 3.00 |
| R LATERAL PELVIS | AP | IN | 8.00 |
| L LATERAL PELVIS | AP | IN | 6.00 |
| MID PELVIS | AP | IN | 9.00 |
| PANCREAS | AP | IN | 7.00 |
| PORTA HEPATIS NODE | AP | IN | 10.50 |
| RM BACKGROUND | | | 4.33 |

Tumor/Background Ratio:
1 - 7.40
(2) - 0.98

We claim:

1. In a surgical procedure wherein an animal suspected of containing neoplastic tissue is surgically accessed and the tissue therein examined visually and by palpation for evidence of neoplastic tissue, the improved methodology which comprises:
   (a) administering to said animal an effective amount of a labelled antibody specific for neoplastic tissue and being labelled with a radioactive isotope exhibiting photon emissions of select energy levels;
   (b) delaying said surgery for a time interval following said administering for permitting said labelled antibody to preferentially concentrate in any neoplastic tissue present in said animal and for the unbound labelled antibody in the blood pool to be cleared to a blood pool background level, so as to increase the ratio of photon emissions from neoplastic tissue to background photon emissions in said animal;
   (c) after said delaying, surgically accessing the operative field of said animal;
   (d) determining the background photon emission count for tissue within said operative filed which is to be examined for neoplastic tissue;
   (e) manually positioning a hand-held probe within said operative field adjacent tissue suspected of being neoplastic, said probe configured for facile hand positioning and maneuvering within said operative field of said animal and characterized by having a collimatable radiation detector having a selective photon entrance and having an output deriving discrete signals responsive to photon emissions when said entrance is positioned immediately adjacent thereto, amplifier means having an input coupled with said radiation detector output pulses, and readout means responsive tos aid output pulses and actuable to an initial condition for commencing the provision of a perceptible indication of an inidica corresponding to the number of said output pulses received;
   (f) determining from said perceptible indication the extent of tissue exhibiting a number of said output pulses having a value above said background output pulses for tissue within said operative field as determined in step (d); and
   (g) surgically removing a sample of said tissue determined in step (f) for histological analysis of said sample.

2. The surgical procedure of claim 1 wherein said perceptible output comprises sound.

3. The surgical procedure of claim 1 wherein said antibody is selected from the group consisting of a whole polyclonal antibody, a whole monoclonal antibody, a fragment antibody, or mixtures thereof.

4. The surgical procedure of claim 1 wherein said isotope exhibits select energy levels of not above about 300 kev.

5. The surgical procedure of claim 1 wherein said surgery is delayed for a time period of at least about 7 days.

6. In a surgical procedure wherein an animal suspected of containing neoplastic tissue is surgically accessed and the tissue therein examined visually and by palpation for evidence of neoplastic tissue, the improved methodology which comprises:
(a) administering to said animal an effective amount of a labelled antibody specific for neoplastic tissue and being labelled with a radioactive isotope exhibiting photon emissions of select energy levels;
(b) delaying said surgery for a time interval following said administering for permitting said labelled antibody to preferentially concentrate in any neoplastic tissue present in said animal and for the unbound labelled antibody in the blood pool to be cleared to a blood pool background level, so as to increase the ratio of photon emissions from neoplastic tissue to background photon emissions in said animal;
(c) after said delaying, surgically accessing the operative field of said animal;
(d) determining tissue within the operative field which is suspected of being neoplastic;
(e) surgically removing a sample of said tissue determined in step (d);
(f) manually positioning a hand-held probe adjacent said removed tissue suspected of being neoplastic, said probe characterized by having a collimatable radiation detector having a selective photon entrance and having an output deriving discrete signals responsive to photon emissions when said entrance is positioned immediately adjacent thereto, amplifier means having an input coupled with said radiation detector output and responsive to said discrete signals to provide corresponding amplified output pulses, and readout means responsive to said output pulses and actuable to an initial condition for commencing the provision of a perceptible indication of an indicia corresponding to the number of said output pulses received; and
(g) determining from said perceptible indication the extent of any tissue in said sample which exhibits a number of said output pulses having a value above background.

7. The surgical procedure of claim 6 wherein tissue determined in step (g) then is subjected to histological analysis.

8. The surgical procedure of claim 6 wherein for a sample which is determined to be neoplastic in step (g), tissue in said animal adjacent said sample is surgically removed.

9. The surgical procedure of claim 6 wherein said perceptible output is selected from the group consisting of sound, light, a chart, or combinations thereof.

10. The surgical procedure of claim 6 wherein said antibody is selected from the group consisting of a whole polyclonal antibody, a whole monoclonal antibody, a fragment antibody, or mixtures thereof.

11. The surgical procedure of claim 6 wherein said isotope exhibits select energy levels of not above about 300 kev.

12. The surgical procedure of claim 6 wherein said surgery is delayed for a time period of at least about 7 days.

13. In a surgical procedure wherein an animal suspected of containing neoplastic tissue is surgically accessed and the tissue therein examined visually and by palpation for evidence of neoplastic tissue, the improved methodology which comprises:
(a) administering to said animal an effective amount of a labelled antibody specific for neoplastic tissue and being labelled with a radioactive isotope exhibiting photon emissions of select energy levels;
(b) delaying said surgery for a time interval following said administering for permitting said labelled antibody to preferentially concentrate in any neoplastic tissue present in said animal and for the unbound labelled antibody in the blood pool to be cleared to a blood pool background level, so as to increase the ratio of photon emissions from neoplastic tissue to background photon emissions in said animal;
(c) after said delaying, surgically accessing the operative field of said animal;
(d) determining the background photon emission count for tissue within said operative field which is to be examined for neoplastic tissue;
(e) manually positioning a hand-held probe within said operative field adjacent tissue suspected of being neoplastic, said probe configured for facile hand positioning and maneuvering within said operative field of said animal and characterized by having a collimatable radiation detector having a selective photon entrance and having an output deriving discrete signals responsive to photon emissions when said entrance is positioned immediately adjacent thereto, amplifier means having an input coupled with said radiation detector output and responsive to said discrete signals to provide corresponding amplified output pulses and readout means responsive to said output pulses and actuable to an initial condition for commencing the provision of a perceptible indication of an indicia corresponding to the number of said output pulses received;
(f) determining from said perceptible indication the extent of tissue exhibiting a number of said output pulses having a value above said background output pulses for tissue within said operative field as determined in step (d);
(g) surgically removing said tissue determined in step (f);
(h) manually positioning said probe adjacent said tissue surrounding said surgically removed tissue to determine from said perceptible indication whether any of said surrounding tissue exhibits a number of output pulses having a value above said tissue background output pulses;
(i) surgically removing any tissue determined in step (h); and
(j) repeating steps (h) and (i) until no more tissue is determined.

14. The surgical procedure of claim 13 wherein said perceptible output comprises sound.

15. The surgical procedure of claim 13 wherein said antibody is selected from the group consisting of a whole polyclonal antibody, a whole monoclonal antibody, a fragment antibody, or mixtures thereof.

16. The surgical procedure of claim 13 wherein said isotope exhibits select energy levels of not above about 300 kev.

17. The surgical procedure of claim 16 wherein said select energy levels are not above about 150 kev.

18. The surgical procedure of claim 13 wherein said isotope is selected from the group consisting of Iodine 131, Iodine 125, Indium 111, Selenium 75, Cobalt 57, and mixtures thereof.

19. The surgical procedure of claim 13 wherein said surgery is delayed for a time period of at least about 7 days.

20. The surgical procedure of claim 19 wherein said surgery is delayed for a time interval ranging from about 7 to 21 days.

* * * * *